United States Patent
Grosso et al.

(10) Patent No.: US 7,230,150 B2
(45) Date of Patent: *Jun. 12, 2007

(54) ZONE REACTOR

(75) Inventors: Philip Grosso, Auburn, CA (US);
Jeffrey H. Sherman, Sebastian, FL (US); Eric W. McFarland, Santa Barbara, CA (US)

(73) Assignee: GRT, Inc., Santa Barbara, CA (US)

( * ) Notice: Subject to any disclaimer, the term of this patent is extended or adjusted under 35 U.S.C. 154(b) by 323 days.

This patent is subject to a terminal disclaimer.

(21) Appl. No.: 10/894,165

(22) Filed: Jul. 19, 2004

(65) Prior Publication Data

US 2004/0267074 A1    Dec. 30, 2004

Related U.S. Application Data

(63) Continuation-in-part of application No. 10/369,148, filed on Feb. 19, 2003, which is a continuation of application No. 10/114,579, filed on Apr. 2, 2002, now Pat. No. 6,525,230, which is a continuation-in-part of application No. 09/951,570, filed on Sep. 11, 2001, now Pat. No. 6,462,243.

(60) Provisional application No. 60/284,642, filed on Apr. 18, 2001.

(51) Int. Cl.
C07C 1/26    (2006.01)

(52) U.S. Cl. ................................ 585/323; 585/641

(58) Field of Classification Search ............... 585/323, 585/641
See application file for complete search history.

(56) References Cited

U.S. PATENT DOCUMENTS

| 3,172,915 A | 3/1965 | Borkowski et al. |
| 3,273,964 A | 9/1966 | Rosset |
| 3,310,380 A | 3/1967 | Lester |
| 3,353,916 A | 11/1967 | Lester ..................... 23/216 |
| 3,894,107 A | 7/1975 | Butter et al. ............... 260/668 |
| 4,006,169 A | 2/1977 | Anderson et al. .......... 260/348 |
| 4,301,253 A | 11/1981 | Warren ..................... 518/700 |
| 4,333,852 A | 6/1982 | Warren ..................... 252/429 |
| 4,373,109 A | 2/1983 | Olah ......................... 585/640 |
| 4,440,871 A | 4/1984 | Lok et al. .................. 502/214 |
| 4,465,893 A | 8/1984 | Olah ......................... 585/709 |
| 4,496,752 A | 1/1985 | Gelbein et al. ............ 549/521 |
| 4,513,092 A | 4/1985 | Chu et al. .................... 502/71 |
| 4,523,040 A | 6/1985 | Olah ......................... 568/671 |
| 4,654,449 A | 3/1987 | Chang et al. .............. 570/261 |
| 4,769,504 A | 9/1988 | Noceti et al. .............. 585/415 |
| 4,795,843 A | 1/1989 | Imai et al. .................. 585/408 |
| 4,982,024 A | 1/1991 | Lin et al. .................... 570/262 |
| 5,087,786 A | 2/1992 | Nubel et al. ............... 585/500 |
| 5,243,098 A | 9/1993 | Miller et al. ............... 568/893 |
| 5,276,240 A | 1/1994 | Timmons et al. |
| 5,334,777 A | 8/1994 | Miller et al. ............... 568/859 |
| 5,486,627 A | 1/1996 | Quarderer, Jr. et al. .... 549/521 |
| 5,998,679 A | 12/1999 | Miller ....................... 568/859 |
| 6,403,840 B1 | 6/2002 | Zhou et al. ................. 568/579 |
| 6,452,058 B1 | 9/2002 | Schweizer et al. ......... 570/223 |
| 6,465,696 B1 | 10/2002 | Zhou et al. ................. 568/671 |
| 6,465,699 B1 | 10/2002 | Grosso ....................... 568/893 |
| 6,472,572 B1 | 10/2002 | Zhou et al. ................. 568/893 |
| 6,486,368 B1 | 11/2002 | Zhou et al. ................. 568/893 |
| 6,525,230 B2 | 2/2003 | Grosso ....................... 568/891 |
| 6,713,087 B2 | 3/2004 | Tracy et al. ................ 424/486 |

(Continued)

FOREIGN PATENT DOCUMENTS

BR    0210054    8/2004

(Continued)

OTHER PUBLICATIONS

Ionic Bromination of Ethane and Other Alkanes (Cycloalkanes) with Bromine Catalyzed by the Polyhalomethane 2AlBr3 Aprotic Organic Superacids under Mild Conditions; Irena S. Akhren, et al.; Tetrahedron Letters, vol. 36, No. 51, pp. 9365-9368, 1995.

(Continued)

Primary Examiner—Thuan Dinh Dang
(74) Attorney, Agent, or Firm—Christie, Parker & Hale, LLP.

(57) ABSTRACT

In a method of converting alkanes to their corresponding alcohols, ethers, olefins, and other hydrocarbons, a vessel comprises a hollow, unsegregated interior defined first, second, and third zones. In a first embodiment of the invention oxygen reacts with metal halide in the first zone to provide gaseous halide; halide reacts with the alkane in the second zone to form alkyl halide; and the alkyl halide reacts with metal oxide in the third zone to form a hydrocarbon corresponding to the original alkane. Metal halide from the third zone is transported through the vessel to the first zone and metal oxide from the first zone is recycled to the third zone. A second embodiment of the invention differs from the first embodiment in that metal oxide is transported through the vessel from the first zone to the third zone and metal halide is recycled from the third zone to the first zone. In a third embodiment of the invention the flow of gases through the vessel is reversed to convert the metal oxide back to metal halide and to convert the metal halide back to the metal oxide.

37 Claims, 17 Drawing Sheets

U.S. PATENT DOCUMENTS

| | | | |
|---|---|---|---|
| 2002/0198416 A1 | 12/2002 | Zhou et al. | 568/910 |
| 2003/0069452 A1 | 4/2003 | Sherman et al. | 568/694 |
| 2003/0078456 A1 | 4/2003 | Yilmaz et al. | 568/488 |
| 2003/0120121 A1 | 6/2003 | Sherman et al. | 568/800 |
| 2003/0125585 A1 | 7/2003 | Yilmaz et al. | 568/490 |
| 2003/0166973 A1 | 9/2003 | Zhou et al. | 568/488 |
| 2004/0006246 A1 | 1/2004 | Sherman et al. | 568/470 |

FOREIGN PATENT DOCUMENTS

| | | |
|---|---|---|
| CA | 2447761 | 11/2002 |
| CA | 2471295 | 7/2003 |
| EP | 1395536 | 3/2004 |
| EP | 1404636 | 4/2004 |
| EP | 1435349 | 7/2004 |
| EP | 1474371 | 11/2004 |
| JP | 2004-529189 | 9/2004 |
| WO | WO 00/07718 | 2/2000 |
| WO | WO 00/09261 | 2/2000 |
| WO | WO 02/094751 | 11/2002 |
| WO | WO 03/000635 | 1/2003 |
| WO | WO 03/022827 | 3/2003 |
| WO | WO 03/062172 | 7/2003 |

OTHER PUBLICATIONS

Selective bromination of alknanes and arylalkanes with CBr4; Vladimir V. Smirnov, eet al., Mendeleev Communications Electronic Version, Issue 5, 2000 (pp. 167-206).

Selective Monohalogenation of Methane over Supported Acid or Platinum Metal Catalysts and Hydrolysis of Methyl Halides over y-Alumina-Supported Metal Oxide/Hydroxide Catalysts. A Feasible Path for the Oxidation Conversion of Methane into Methyl Alcohol/ Dimethyl Ether; George B. Olah, et al.; Contribution from the Donald P. and Katherine B. Loker Hydrocarbon Research Institute and Department of Chemistry, University of Southern California, Los Angeles, CA; received Apr. 22, 1985 (J. Am. Chem. Soc. 1985, 107, 7097-7105).

Electrophilic Methane Conversion; by George A. Olah; Acc. Chem. Res. 1987, 20, 422-428, Loker Hydrocarbon Research Institute and Department of Chemistry, University of Southern California, Los Angeles, California.

Antimony Pentafluoride/Graphite Catalyzed Oxidation Carbonylation of Methyl Halides with Carbon Monoxide and Copper Oxides (or Copper/Oxygen) to Methyl Acetate; by George A. Olah and Jozef Bukala; J. Org. Chem., 1990, 55, No. 14, 4293-4297; Donald P. and Katherine B. Loker Hydrocarbon Research Institute and Department of Chemistry, University of Southern California, University Park, Los Angeles, California.

Superacid-Catalyzed Carbonylation of Methane, Methyl Halides, Methyl Alcohol, and Dimethyl Ether to Methyl Acetate a Acetic Acide; by Alessandro Bagno, Jozef Bukala, and George A. Olah; J. Org. Chem. 1990, vol. 55, No. 14, 4284-4292; Donald P. and Katherine B. Loker Hydrocarbon Research Institute, University of Southern California, University Park, Los Angeles, California.

Ylide chemistry. 1. Bifunctional acid-base-catalyzed conversion of heterosubstituted methanes into ethylene and derived hydrocarbons. The onium-ylide mechanism of the C1→C2 conversion by George A. Olah et al. (J. Am. Chem. Soc. 106, 2143-2149 (1984).

Grignard Reagents with Transition Metal Halides: Disproportionation, and Exchange with Olefins; by Masuhiko Tamura and Jay K. Kochi, Bulletin of the Chemical Society of Japan, v. 44, 1971 pp. 3063-3073.

The Catalytic Dehydrohalogenation of Haloethanes on Solid Acids and Bases, Mochida, et al., Bulletin of the Chemical Society of Japan, vol. 44, 3305-3310, 1971.

Nanocrystalline Ultra High Surface Area Magnesium Oxide as a Selective Base Catalyst, Ryan Richards, et al., Scripta Materialia, 44, 2001, pp. 1663-1666.

Nanocrystal Metal Oxide-Chlorine Adducts: Selective Catalysts for Chlorination of Alkanes, Naijian Sun and Kenneth J. Klabunde, J. Am. Chem. Soc., 1999, 121, 5587-5588.

Nanocrystalline MgO as a Dehydrohalogenation Catalyst, Iiya V. Mishakov, et al., Journal of Catalysis 206, 40-48, 2002.

Changes in Texture and Catalytic Activity of Nanocrystalline MgO during Its Transformation to $MgCl_2$ in the Reaction with 1-Chlorobutane, Kenneth J. Klabunde, et al., J. Phys. Chem. B. 2001, 105, 3937-3941.

http://webbook.nist.gov/.

Monomethyl-Branching of Long n-Alkanes in the Range from Decane to Tetracosane on Pt/H-ZSM-22 Bifunctional Catalyst, Marion C. Claude and Johan A. Martens, Journal of Catalysts 190, pp. 39-48 (2000).

Synthesis and Characterization of a Catalytically Active Nickel-Silicoaluminophosphate Catalyst for the Conversion of Methanol to Ethene; J.M. Thomas, Y Xu, C.R.A. Catlow, and J.W. Couves; Chem. Mater. 1991, 3, 667-672.

Catalytically active centres in porous oxides: design and performance of highly selective new catalysts; John Meurig Thomas and Robert Raja; The Royal Society of Chemistry 2001, Chem. Commun., 2001, 675-687.

C1 Coupling via bromine activation and tandem catalytic condensation and neutralization over CaO/zeolite composites; Ivan Lorkovic, et al.; The Royal Society of Chemistry 2004; Chem. Commun. 2004, pp. 566-567.

Industrial Organic Chemistry; K. Weissermel and H.J. Arpe, 3rd ed., 1997, pp. 160-162, 208.

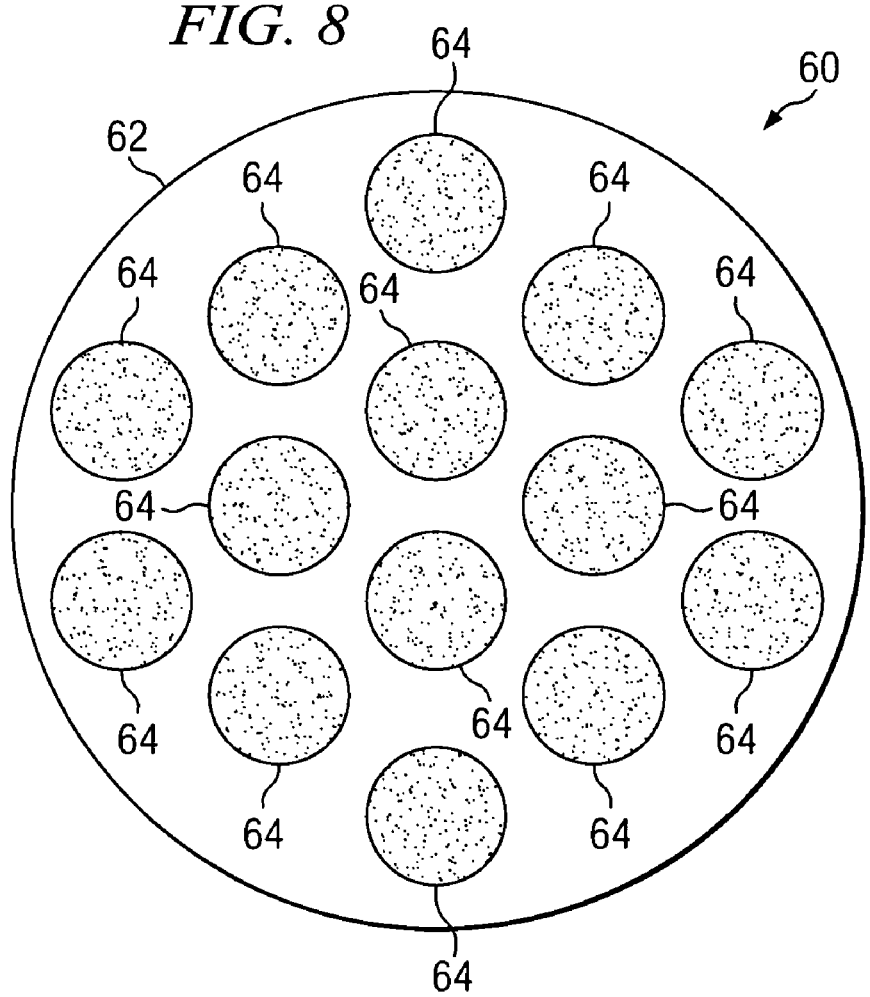

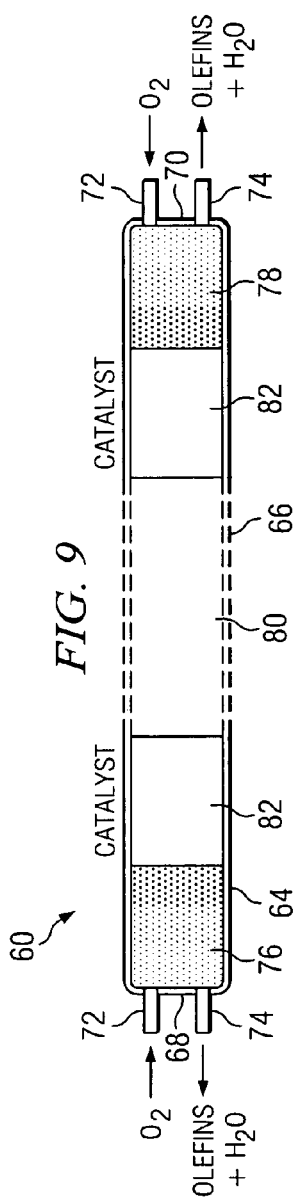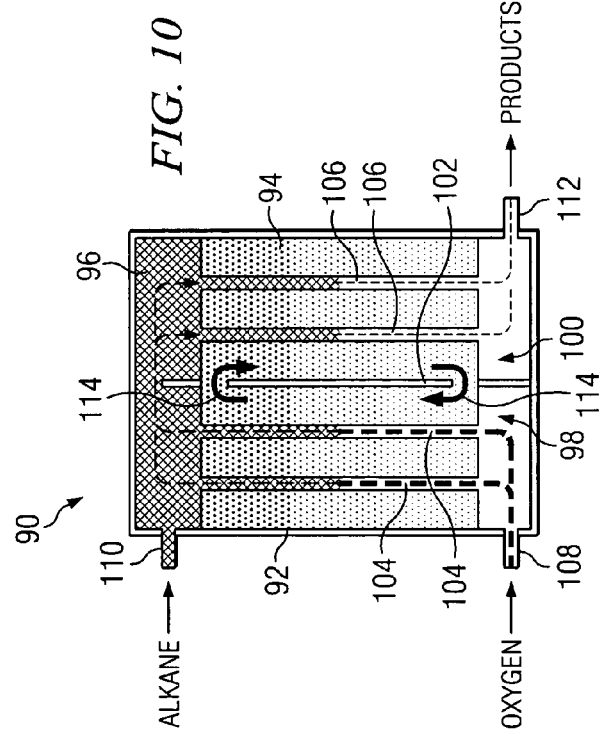

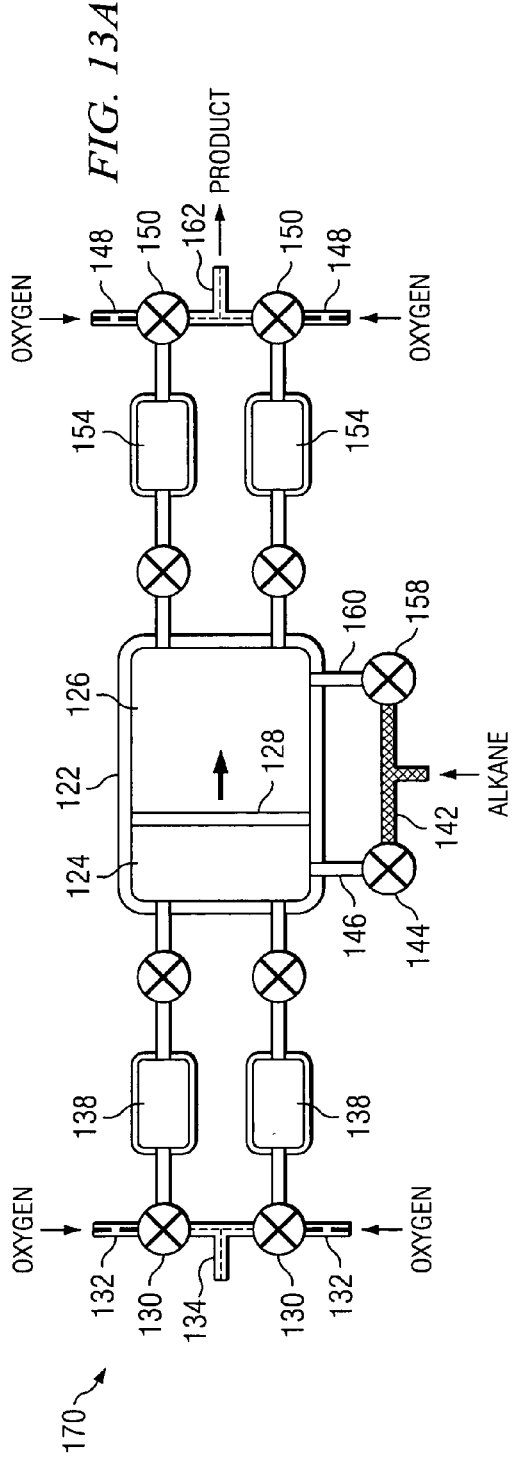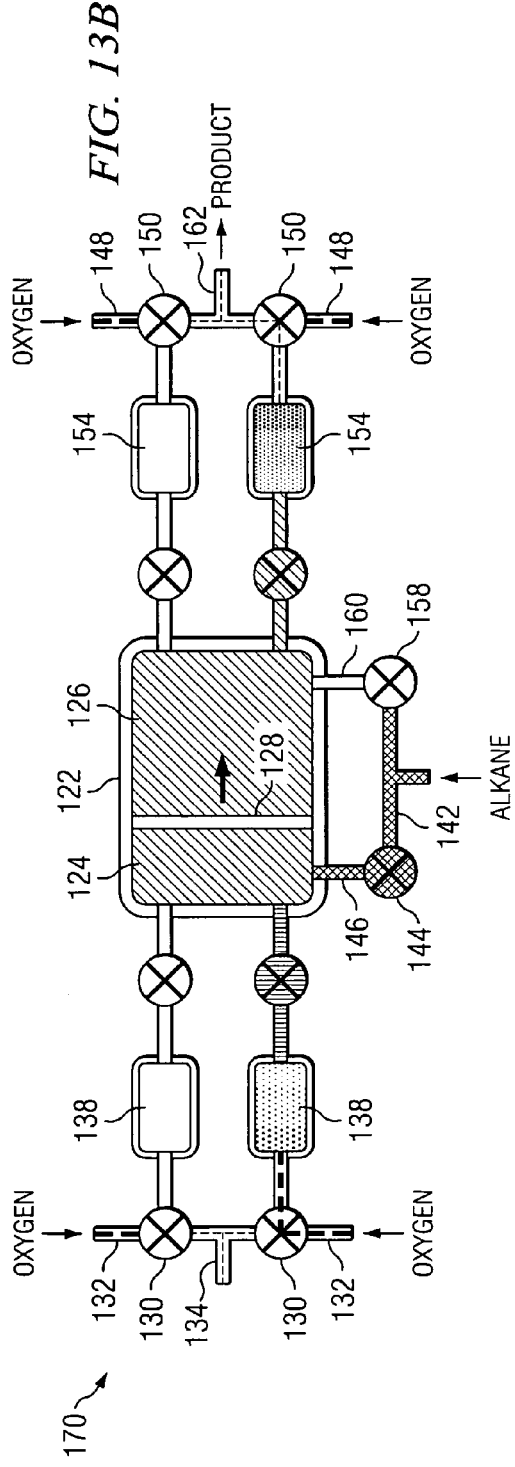

ZONE REACTOR

CROSS-REFERENCE TO RELATED APPLICATIONS

This is a continuation-in-part application under 37 C.F.R. §1.63 of application Ser. No. 10/369,148 filed Feb. 19, 2003, currently pending; which is a continuation application of application Ser. No. 10/114,579, filed Apr. 2, 2002, now U.S. Pat. No. 6,525,230; which is a continuation-in-part application of application Ser. No. 09/951,570 filed Sep. 11, 2001, now U.S. Pat. No. 6,462,243, claiming priority based on provisional application Ser. No. 60/284,642 filed Apr. 18, 2001.

TECHNICAL FIELD

This invention relates to zone reactors, and more particularly to zone reactors that are useful in processes for converting alkanes to alcohols, ethers, olefins, and other hydrocarbons.

BACKGROUND AND SUMMARY OF THE INVENTION

U.S. Pat. No. 6,462,243 discloses a method of converting alkanes to their corresponding alcohols and ethers using bromine. The patent comprises four embodiments of the invention therein disclosed each including a reactor wherein bromine reacts with an alkane to form alkyl bromide and hydrogen bromide, a converter wherein the alkyl bromide formed in the reactor reacts with metal oxide to form the corresponding alcohol or ether, and numerous other individual components.

The present invention comprises zone reactors wherein the several reactions disclosed in the co-pending parent application are carried out in a single vessel. In this manner the overall complexity of the system for converting alkanes to their corresponding alcohols, ethers, olefins, and other hydrocarbons is substantially reduced. In addition, heat generated by reactions occurring in particular zones within the vessel can be utilized to facilitate reactions occurring in other zones.

Various embodiments of the invention are disclosed. In accordance with a first embodiment the zone reactor comprises a countercurrent system wherein gases flow in a first direction and metal compounds flow in the opposite direction. A second embodiment of the invention comprises a cocurrent arrangement wherein the gases and the metal compounds travel in the same direction. The first and second embodiments of the invention are continuous systems as opposed to the third embodiment of the invention which is a fixed-bed system that is continual in operation. In accordance with the third embodiment the metal compounds remain fixed within the vessel while the gases are directed through the vessel first in one direction and later in the opposite direction.

In the following Detailed Description the invention is described in conjunction with the conversion of methane to methanol. However, as will be appreciated by those skilled in the art, the invention is equally applicable to the conversion of ethane and the higher alkanes to their corresponding alcohols, ethers, olefins, and other hydrocarbons.

The following Detailed Description also describes the invention in conjunction with the use of a particular halide, i.e., bromine. However, as will be appreciated by those skilled in the art, the invention is equally applicable to the conversion of alkanes to their corresponding alcohols, ethers, and other hydrocarbons utilizing other halides, including in particular chlorine and iodine.

BRIEF DESCRIPTION OF THE DRAWINGS

A more complete understanding of the present invention may be had by reference to the following Detailed Description when taken in connection with the accompanying Drawings wherein:

FIG. 8 is a sectional view taken along the line 8—8 in FIG. 7 in the direction of the arrows;

FIG. 9 is a diagrammatic illustration of a component part of the apparatus of FIG. 7;

FIG. 10 is a diagrammatic illustration of an apparatus useful in the implementation of a variation of the embodiment of the invention illustrated in FIG. 3;

FIG. 13A is a diagrammatic illustration of a first step in the operation of an apparatus comprising a variation of the apparatus illustrated in FIG. 11;

FIG. 13B is an illustration of a later step in the operation of the apparatus of FIG. 13A;

DETAILED DESCRIPTION OF THE INVENTION

Figure 1:
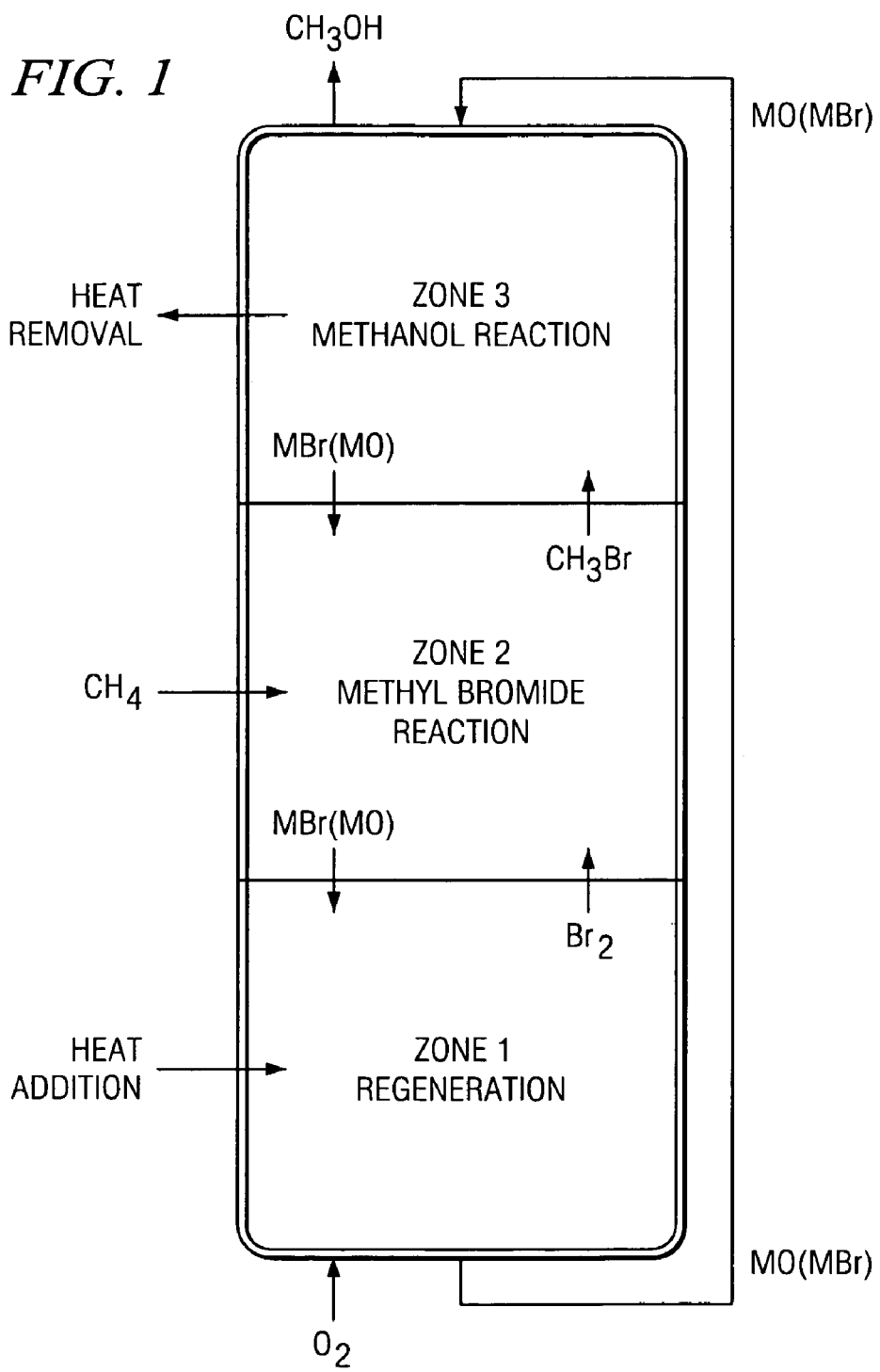
FIG. 1 is a diagrammatic illustration of a countercurrent zone reactor comprising a first embodiment of the invention.

The present invention comprises zone reactors wherein three sequential chemical reactions occur in separate zones within a single vessel. In Zone 1 oxygen is reacted with a metal bromide to form bromine gas and the corresponding metal oxide. Bromine gas from Zone 1 passes to Zone 2 where the second chemical reaction occurs. In Zone 2 methane gas is introduced at an intermediate point in the vessel. Methane reacts with the bromine from Zone 1 to form methyl bromide and hydrogen bromide. The latter gasses pass into Zone 3 where the third chemical reaction causes methyl bromide and hydrogen bromide to react with metal oxide to form methanol and metal bromide. Methanol is converted to the liquid phase by condensation and is recovered from the reactor vessel as a liquid. Excess gasses, mostly methane, are separated from the recovered methanol and are returned to the zone reactor along with fresh methane. Metal oxide from Zone 1 is transported to Zone 3 where it proceeds from Zone 3 through Zone 2 to Zone 1 thereby completing the cycle.

Reactions in Zone 1 are endothermic; therefore, means to supply heat are provided. Zone 2 and Zone 3 involve exothermic reactions; therefore, means to remove heat are provided.

The separation of zones is not necessarily a sharp one since there is no physical barrier between zones. Therefore, some overlap of reactions may occur. The important element, however, is that all the oxygen is converted to metal oxide in Zone 1 so that little or no oxygen remains to react with methane in Zone 2. In Zone 2 other bromides, i.e., higher brominated species, in addition to methyl bromide may form and result in products other than methanol in Zone 3, such as various ethers. Any by-products are separated from methanol in various isolation/purification steps. Any unreacted methane in Zone 2 will pass through Zone 3 and be recycled in Zone 2. Other unreacted brominated species are returned to Zone 2 either for reaction or to suppress further formation of the higher brominated species by satisfying chemical equilibrium.

The zone reactor operates at essentially atmospheric pressure and at temperatures up to about 750F. The principal advantage over conventional methanol process lies in the simplicity of the system. The zone reactor achieves the synthesis of methanol in a single vessel whereas the conventional process requires multiple vessels to first produce synthesis gas followed by catalytic reaction. Furthermore the zone reactor operates at slightly above atmospheric pressure whereas the conventional process requires pressures up to 200 atmospheres.

As will be appreciated by those skilled in the art, the zone reactors of the present invention can be used with ethane and higher alkanes to produce corresponding alcohols, ethers, olefins, and other hydrocarbons.

The zone reactor also has advantages over a multi-step process utilizing the same bromine chemistry. One advantage is that one step replaces several. In addition, bromine gas remains in one vessel and need not be condensed and re-vaporized.

FIG. 1 shows a countercurrent system employing the zone reactor of the present invention. In this embodiment gasses flow upward through a bed of solids which is moving downward. Oxygen is introduced at the bottom of the vessel and reacts with a metal bromide to form bromine gas and the corresponding metal oxide. This step entails regeneration of the metal oxide, which was expended in Zone 3. Bromine from Zone 1 proceeds to Zone 2 where methane gas is introduced. The methane reacts with the bromine to form methyl bromide and hydrogen bromide. The latter two gasses proceed upward to Zone 3 where fresh metal oxide reacts with these gasses to form methanol and metal bromide. The regenerated metal oxide from Zone 1 is returned to Zone 3 thereby completing the cycle.

The reaction in Zone 1 may require heat. If so, a suitable heat supply apparatus is provided. In Zone 2 the reactions are exothermic. Heat from the Zone 2 reactor is allowed to raise the temperature of the gasses formed. Zone 3 involves reactions that may require the removal of heat; therefore, a suitable heat removal apparatus is provided.

Figure 1A:
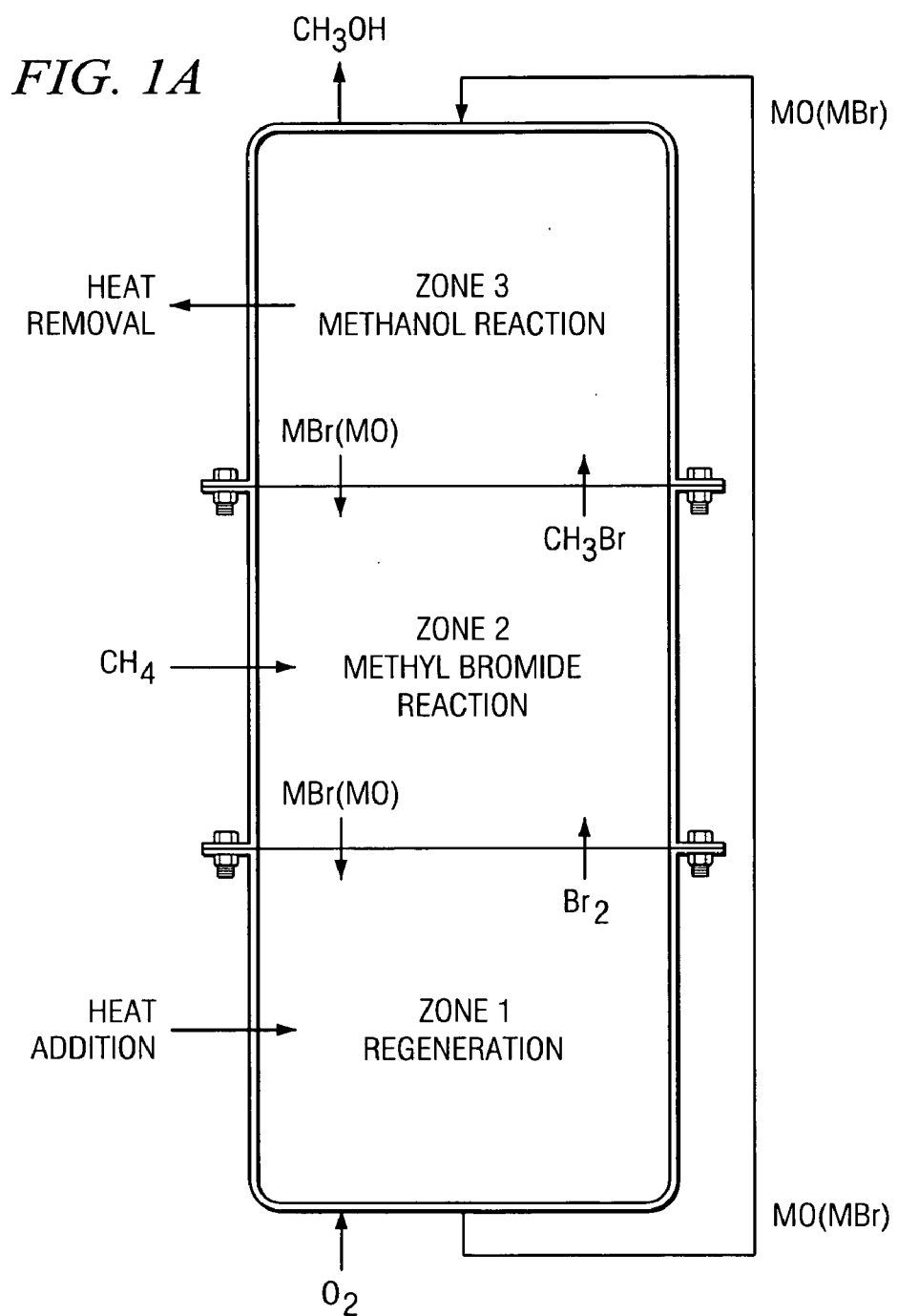
FIG. 1A is an illustration of a variation of the countercurrent zone reactor of FIG. 1.

The zone reactor of FIG. 1 comprises a unitary vessel. Referring to FIG. 1A, the zone reactor of FIG. 1 may also comprise a vessel having multiple components which are secured one to another by suitable fasteners. This allows removal of components of the vessel for cleaning and/or repair.

Figure 2:
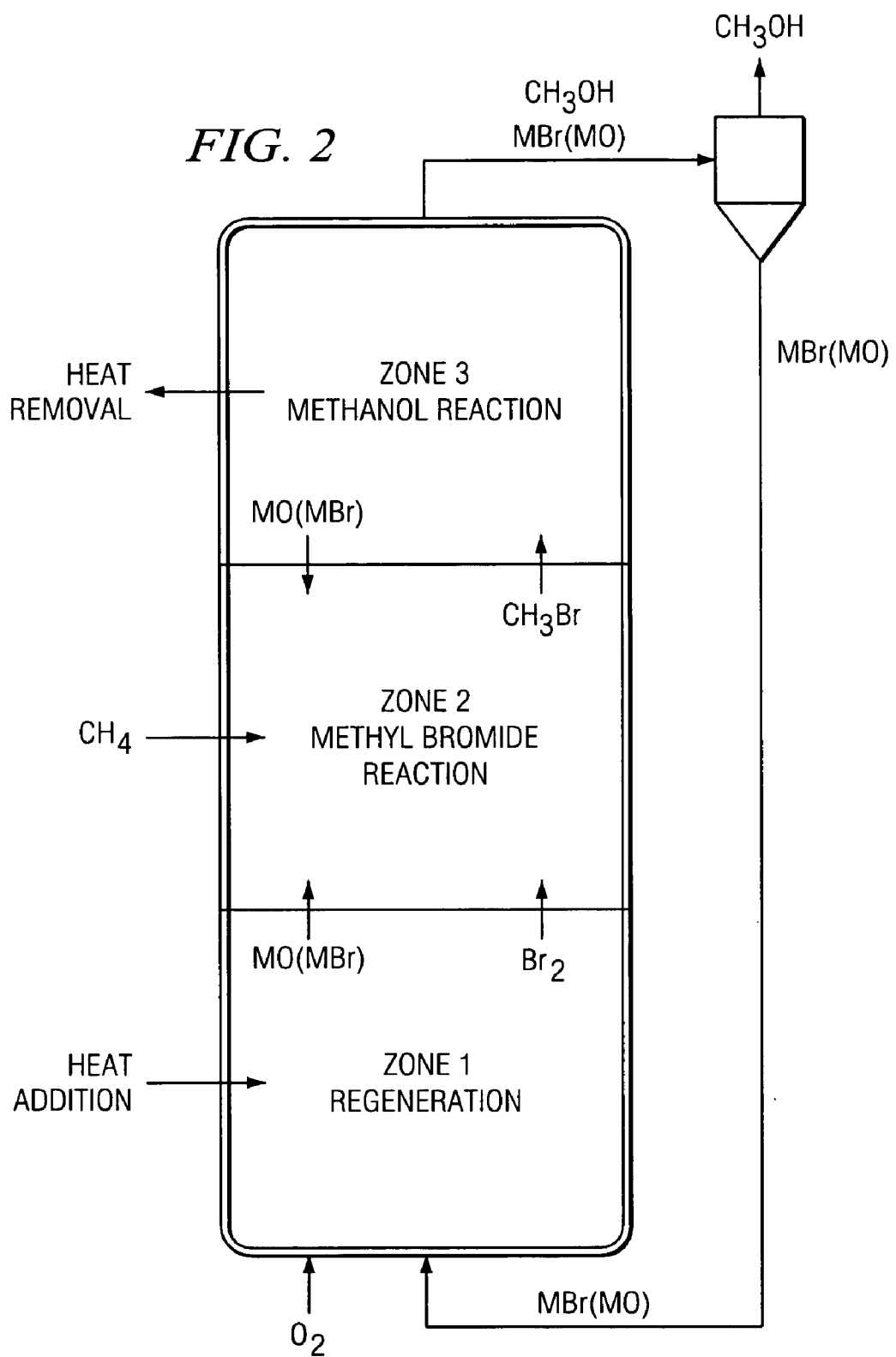
FIG. 2 is a diagrammatic illustration of a cocurrent zone reactor comprising a second embodiment of the invention.

FIG. 2 shows a cocurrent system employing the zone reactor concept. In this system gasses and solids proceed together in the same direction. In addition the solids are suspended in the gas flow in a way such that the gasses transport the solids. This embodiment combines the reaction steps with the physical movement of the solids. The chemical reaction steps are as described for FIG. 1.

Figure 2A:
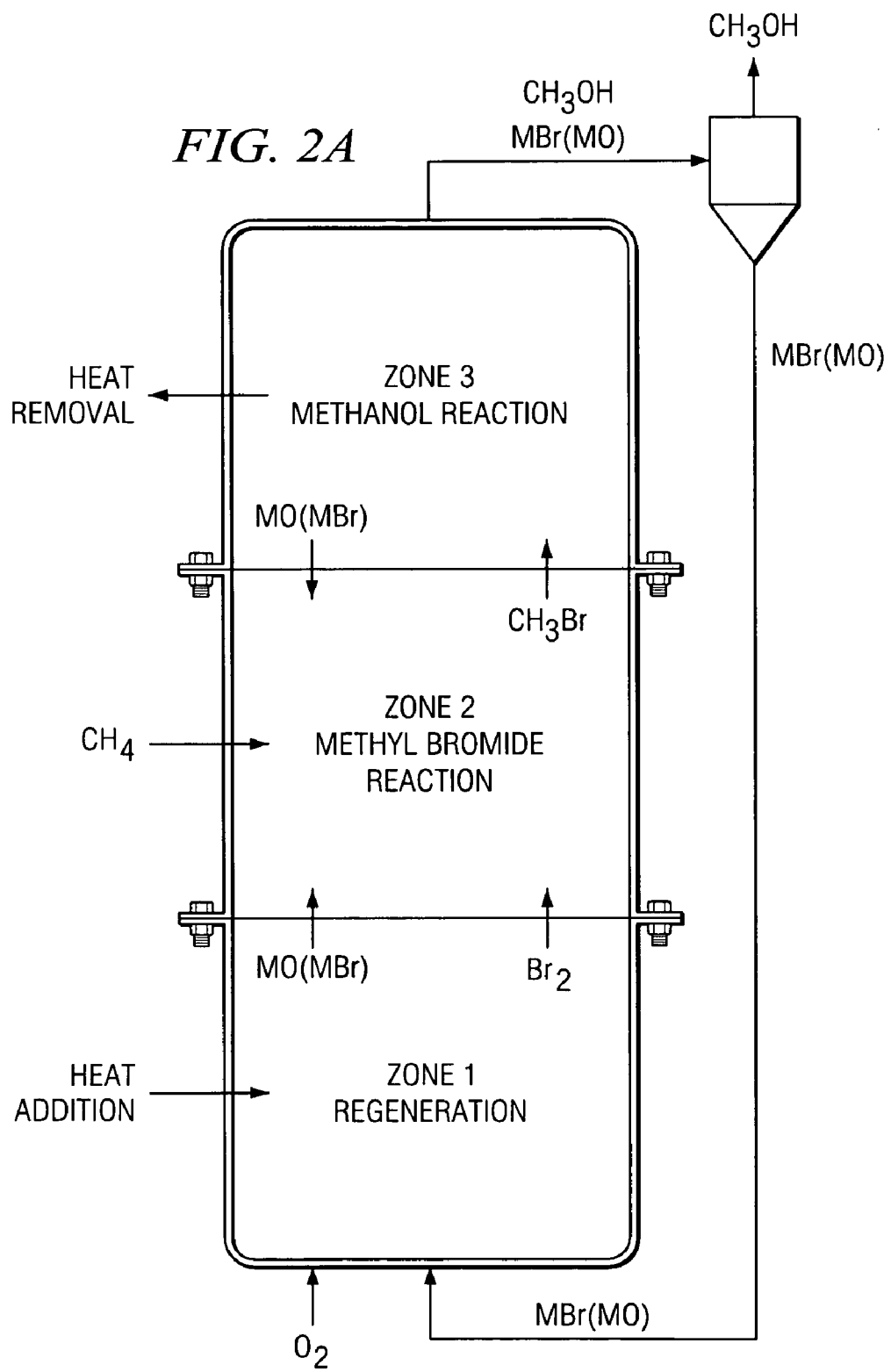
FIG. 2A is an illustration of a variation of the cocurrent zone reactor of FIG. 2.

The zone reactor of FIG. 2 comprises a unitary vessel. Referring to FIG. 2A, the zone reactor of FIG. 2 may also comprise a vessel having multiple components which are secured one to another by suitable fasteners. This allows removal of components of the vessel for cleaning and/or repair.

Figure 3:
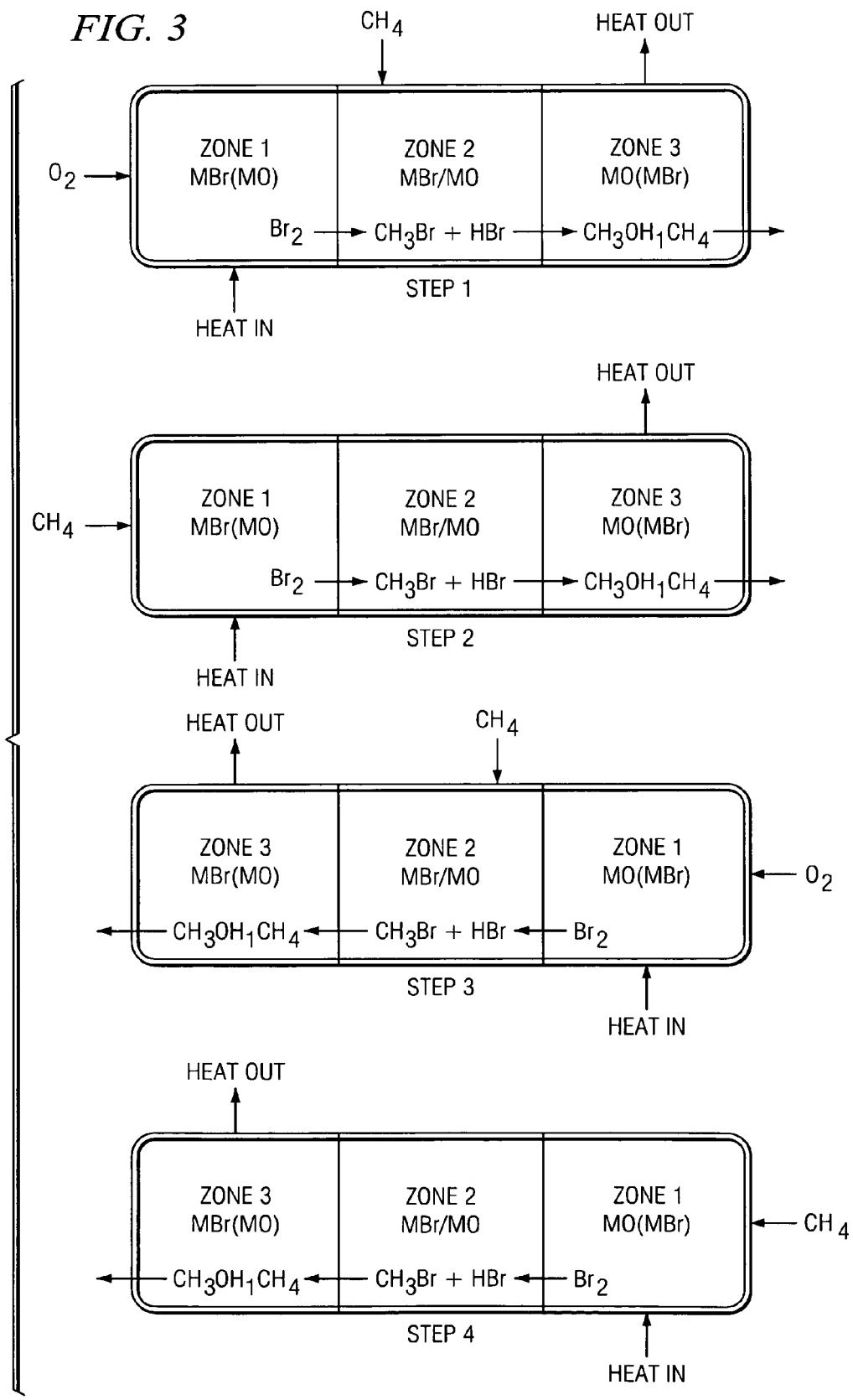
FIG. 3 is a diagrammatic illustration of a fixed bed zone reactor comprising a third embodiment of the invention.

FIG. 3 shows a fixed-bed system comprising a third embodiment of the invention. Whereas FIGS. 1 and 2 describe continuous systems, FIG. 3 describes a continual system. In the system of FIG. 3 the metal bromide/oxide solids remain fixed within the vessel while gasses are passed through the vessel. The regeneration step is carried out in place by reversing the flow of gases through the system. The steps involved and the order in which they are performed are described in FIG. 3. This mode of operation distinguishes itself by avoiding movement of solids as in the embodiments of FIGS. 1 and 2. In addition, by carefully setting the duration of each step the heat generated in Zones 2 and 3 can be at least partially allowed to raise the temperature of the bed. Then, when flow is reversed and Zone 3 becomes Zone 1, the heat stored in the solids can be used to provide the reaction heat needed in Zone 1. In this way the overall effect is a direct transfer of heat from the exothermic zone to the zone where it is needed without going through an intermediate step such as steam generation. However, since the heat generated in Zones 2 and 3 is likely to be greater than that needed in Zone 1, it may still be necessary to remove some heat from the system.

Figure 3A:
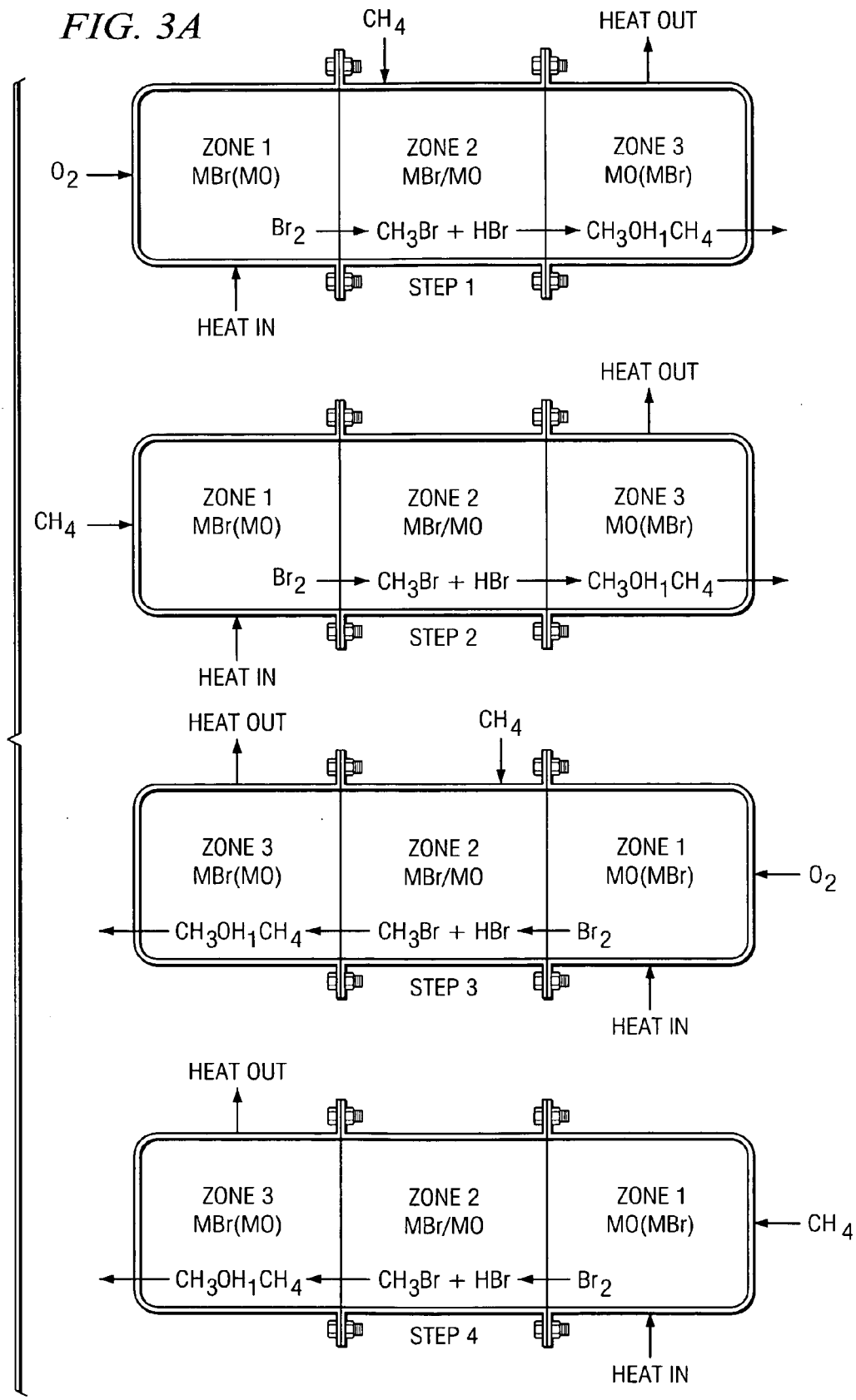
FIG. 3A is an illustration of a variation of the fixed bed zone reactor of FIG. 3.

The zone reactor of FIG. 3 comprises a unitary vessel. Referring to FIG. 3A, the zone reactor of FIG. 3 may also comprise a vessel having multiple components which are secured one to another by suitable fasteners. This allows removal of components of the vessel for cleaning and/or repair.

Figure 14:
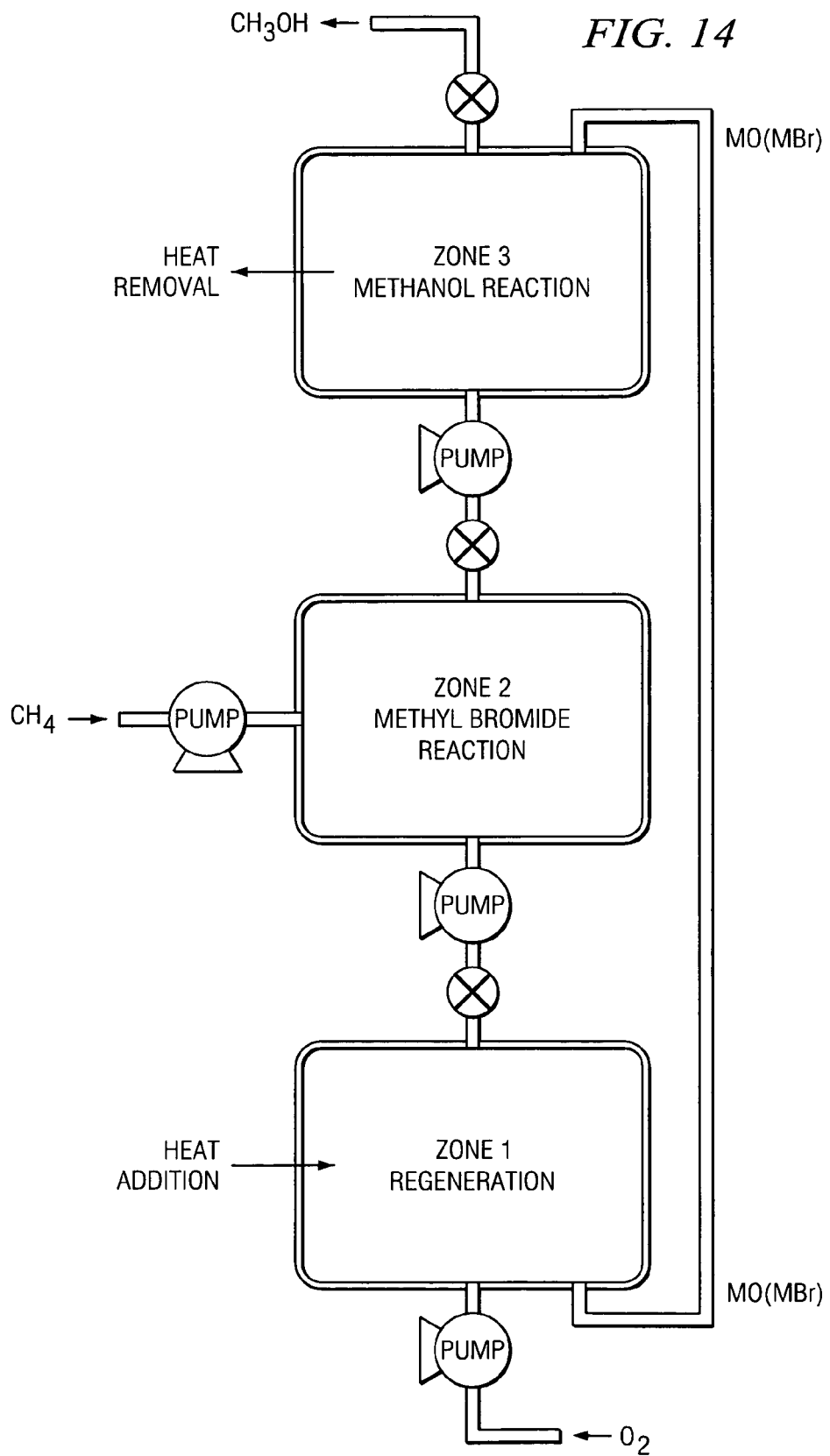
FIG. 14 is a diagrammatic illustration of a zone reactor comprising a fourth embodiment of the invention.

Referring to FIG. 14, the zone reactor of the present invention may also comprise separate vessels. Utilization of separate vessels to define the zone reactor allows the use of pumps to control the pressure at which the reaction within each individual vessel takes place. Utilization of separate vessels also allows the use of valves to prevent outflow from a particular vessel until the reaction therein has been completed and to thereafter facilitate transfer of the action products to the next zone.

The physical separation of the chemical species formed during operation of the zone reactors disclosed herein is accomplished by conventional means, with valuable products and by-products recovered and other useful species returned to the appropriate zone for conversion or satisfaction of chemical equilibrium.

Figure 4A:
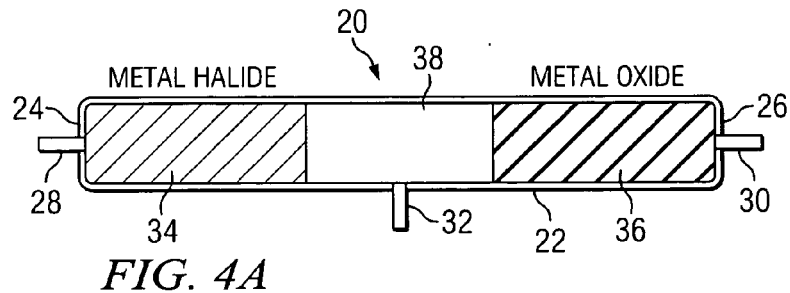
FIG. 4A is a sectional view of an apparatus useful in the practice of the embodiment of the invention shown in FIG. 3.

Referring to FIG. 4A an apparatus 20 is diagrammatically illustrated. The apparatus 20 comprises an imperforate cylinder 22 formed from an appropriate metal, an appropriate polymeric material, or both. The cylinder 22 has closed ends 24 and 26. A passageway 28 extends through the end 24 of the cylinder 22, a passageway 30 extends through the end 26 of the cylinder 22, and a passageway 32 extends to the central portion of the cylinder 22 between the ends 24 and 26 thereof.

The apparatus 20 further comprises a first zone 34 which is initially filled with metal halide. A second zone 36 located at the opposite end of the cylinder 22 from zone 34 is initially filled with metal oxide. A third or central zone 38 which is centrally disposed between the first zone 34 and the second zone 36 is initially empty.

Figure 4B:
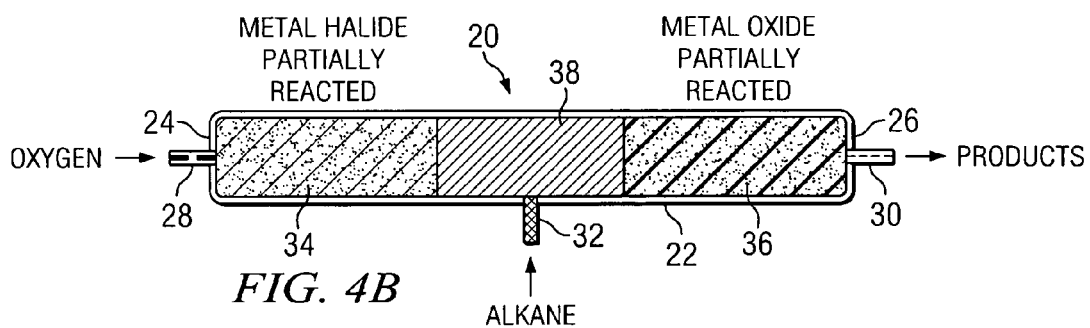
FIG. 4B is an illustration of an early stage in the operation of the apparatus of FIG. 4A.

Referring to FIG. 4B, a first stage in the operation of the apparatus 20 is shown. Oxygen or air is directed into the first zone 34 through the opening 28. The oxygen or the oxygen from the air reacts with the metal halide to produce metal oxide and halide. The halide flows from the first zone 34 into the central zone 38.

Simultaneously with the introduction of oxygen or air into the first zone 34 through the opening 28, a selected alkane is directed into the central zone 38 through the opening 32. Within the central zone 38 halide reacts with alkane to produce alkyl halide and hydrogen halide. The alkyl halide and the hydrogen halide pass from the central zone 38 to the second zone 36.

Within the second zone 36 the alkyl halide and the hydrogen halide react with metal oxide to produce products which are recovered through the passageway 30. The reaction within the second zone 36 also produces metal halide.

Figure 4C:
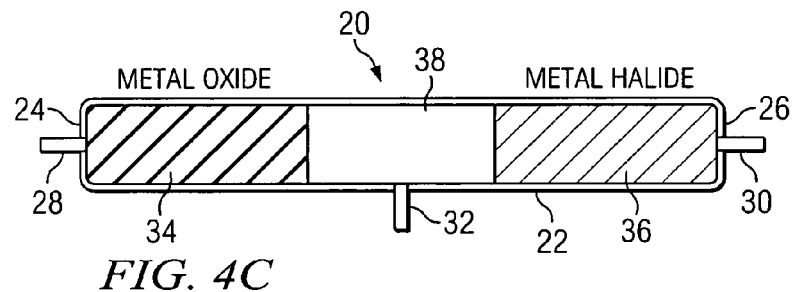
FIG. 4C is an illustration of a later stage in the operation of the apparatus of FIG. 4A.

Referring to FIG. 4C, the foregoing reactions in the first zone 34, the central zone 38, and the second zone 36 continue until substantially all of the metal halide that was originally in the first zone 34 has been converted to metal oxide. Simultaneously, substantially all of the metal oxide that was originally in the second zone 36 is converted to metal halide. At this point the reaction is stopped and the central zone 38 is evacuated.

Figure 4D:
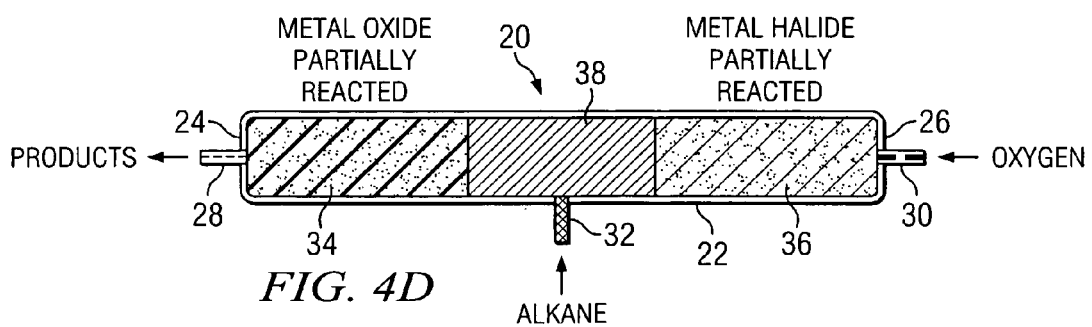
FIG. 4D is an illustration of a still later stage in the operation of the apparatus of FIG. 4A.

The next stage in the operation of the apparatus 20 is illustrated in FIG. 4D. The reactions described above in conjunction in conjunction with FIG. 4B are now reversed, with oxygen or air being admitted to the second zone 36 through the opening 30. The oxygen or oxygen from the air reacts with the metal halide in the second zone 36 to produce halide and metal oxide. The halide from the reaction in the second zone 36 passes to the central zone 38 where it reacts with alkane received through the opening 32 to produce alkyl halide and hydrogen halide. Alkyl halide and hydrogen halide from the reaction within the central zone passed to the first zone 34 where they react with the metal oxide contained therein to produce product and metal halide. The reactions continue until substantially all of the metal halide in the second zone has been converted to metal oxide and substantially all of the metal oxide within the first zone 34 has been converted to metal halide at which time the apparatus 20 is returned to the configuration of FIG. 4A. At this point the central zone 38 is evacuated and the above described cycle of operation is repeated.

Figure 5:
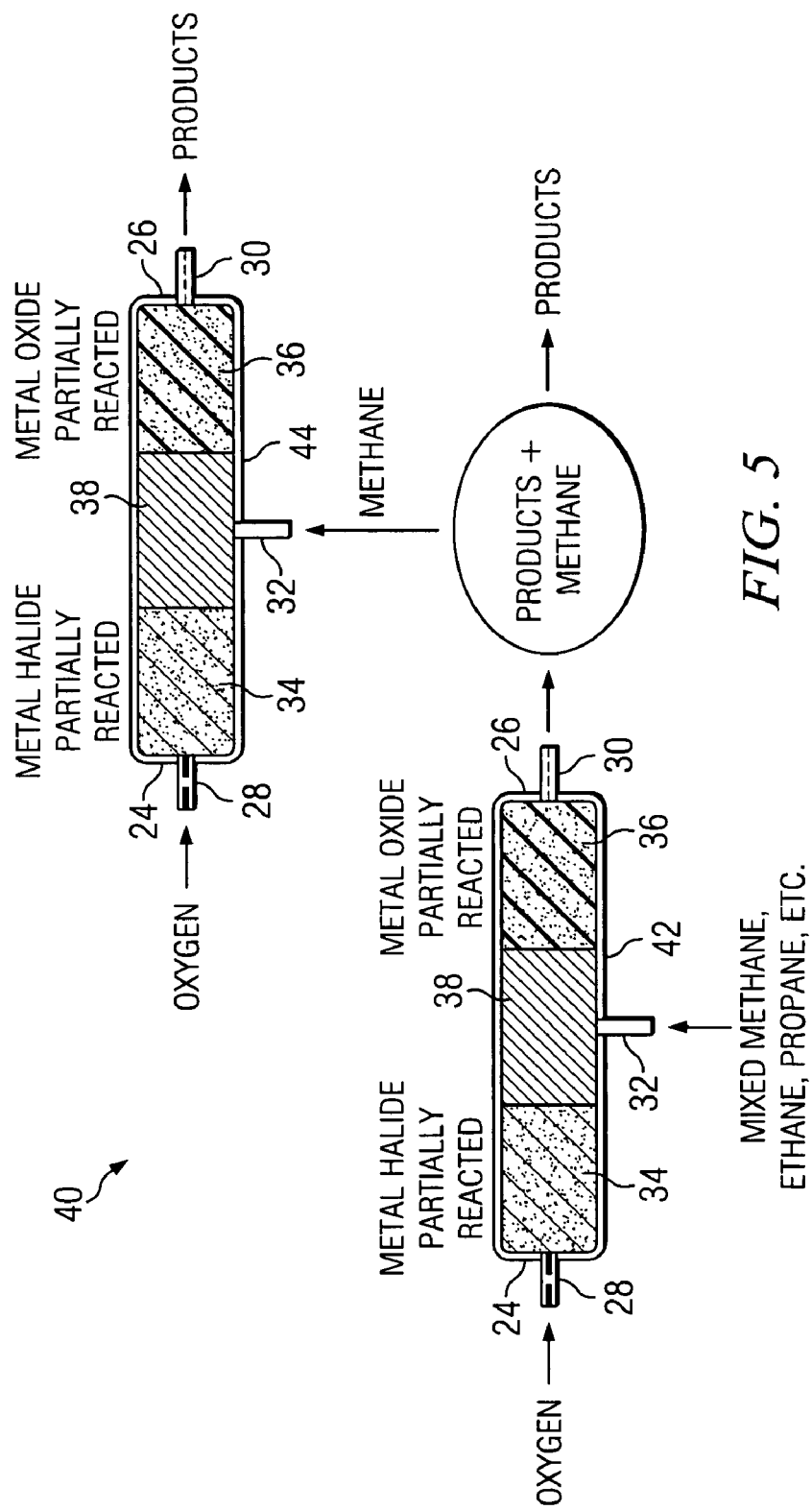
FIG. 5 is a diagrammatic illustration of the use of the apparatus of FIG. 4A in the conversion of mixtures of alkanes to chemically related products.

Referring to FIG. 5 there is shown an apparatus 40 useful in the practice of the third embodiment of the invention as illustrated in FIG. 3 and described hereinabove in conjunction therewith. Many of the component parts of the apparatus 40 are identical in construction and function to component parts of the apparatus 20 illustrated in FIGS. 4A–4B, inclusive, and described hereinabove in conjunction therewith. Such identical component parts are designated in FIG. 5 with the same reference numerals utilized in the foregoing description of the apparatus 20.

The apparatus 40 comprises first and second cylinders 42 and 44. The cylinders 42 and 44 are each identical in construction and function to the cylinder 22 illustrated in FIGS. 4A–4D, inclusive, and described above in conjunction therewith. The cylinder 42 receives a mixture of alkanes, including methane, ethane, propane, etc., through the opening 32 thereof. The several reactions that occur within the cylinder 42 produce products and methane which are initially recovered through the opening 30.

The methane resulting from the reactions which occur within the cylinder 42 is separated from the products resulting from the reactions within the cylinder 42 by conventional techniques such as distillation. The methane is then directed into the cylinder 44 through the opening 32 thereof. Within the cylinder 44 the methane is converted to products utilizing the same reactions described above in conjunction with the apparatus 20. Products resulting from the reactions occurring within the cylinder 44 are initially recovered through the opening 30 thereof.

As will be understood by reference to the foregoing description of the operation of the apparatus 20, operation of the apparatus 40 continues until substantially all of the metal halide that was originally in the first zones 34 of the cylinders 42 and 44 has been converted to metal oxide and until substantially all of the metal oxide that was originally in the second zones 36 of the cylinders 42 and 44 has been converted to metal halide. At this point the direction of flow through the cylinders 42 and 44 is reversed. That is, oxygen is directed into the cylinders 42 and 44 through the passageways 30, products and methane are recovered from the cylinder 42 through the passageway 28, and products are recovered from the cylinder 44 through the passageway 28.

Figure 6A:
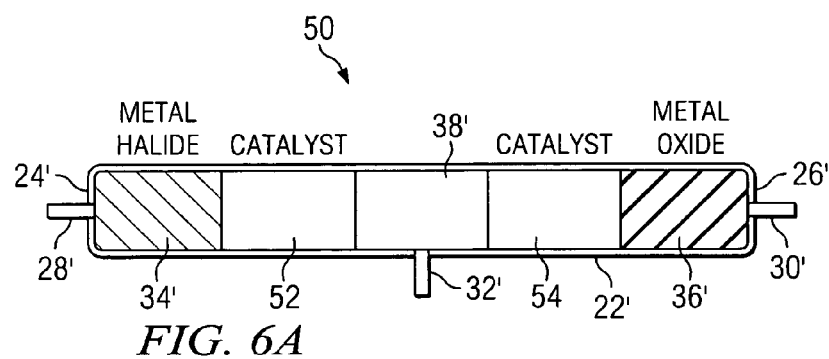
FIG. 6A is a sectional view diagrammatically illustrating an apparatus useful in practicing a variation of the embodiment of the invention illustrated in FIG. 3.

Referring to FIG. 6A, there is shown an apparatus 50 useful in the practice of a variation of the third embodiment of the invention as illustrated in FIG. 3 and described hereinabove in conjunction therewith. Many of the component parts of the apparatus 50 are substantially identical in construction and function to component parts of the apparatus 20 illustrated in FIGS. 4A–4D, inclusive, and described hereinabove in conjunction therewith. Such substantially identical component parts are designated in FIGS. 6A and 6B with the same reference numerals utilized above in the description of the apparatus 20 but are differentiated there from by means of a prime (') designation.

The apparatus 50 differs from the apparatus 20 of FIGS. 4A–4D, inclusive, in that the cylinder 22' of the apparatus 50 includes additional zones 52 and 54 therein. Each of the zones 52 and 54 receives a catalyst the function of which is to facilitate coupling of the alkyl halide molecules produced by the reaction occurring within the central zone 38' thereby producing products comprising higher numbers of carbon atoms than would otherwise be the case. Preferably the catalyst that is contained within the zones 52 and 54 is a selected zeolite. However, the catalyst received within the zones 52 and 54 may also comprise a metal halide/oxide. If a metal halide/oxide is employed within the zones 52 and 54, it preferably comprises a different metal halide/oxide as compared with the metal halide/oxide that is utilized in the zones 34 and 36. Operation of the apparatus 50 proceeds identically to the operation of the apparatus 20 as described above except that the presence of a catalyst in the zones 52 and 54 facilitates coupling of the alkyl halide molecules produced within the zone 38 to products.

Figure 6B:
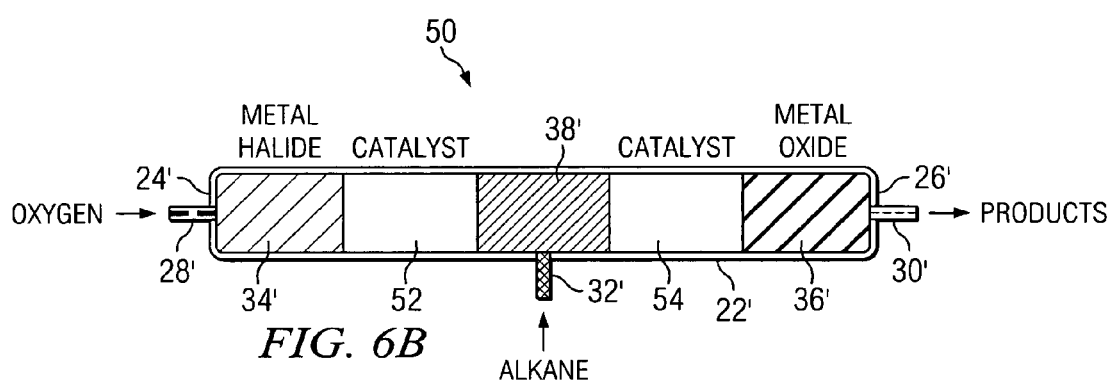
FIG. 6B is a diagrammatic illustration of the utilization of the apparatus of FIG. 6A.
Figure 7:
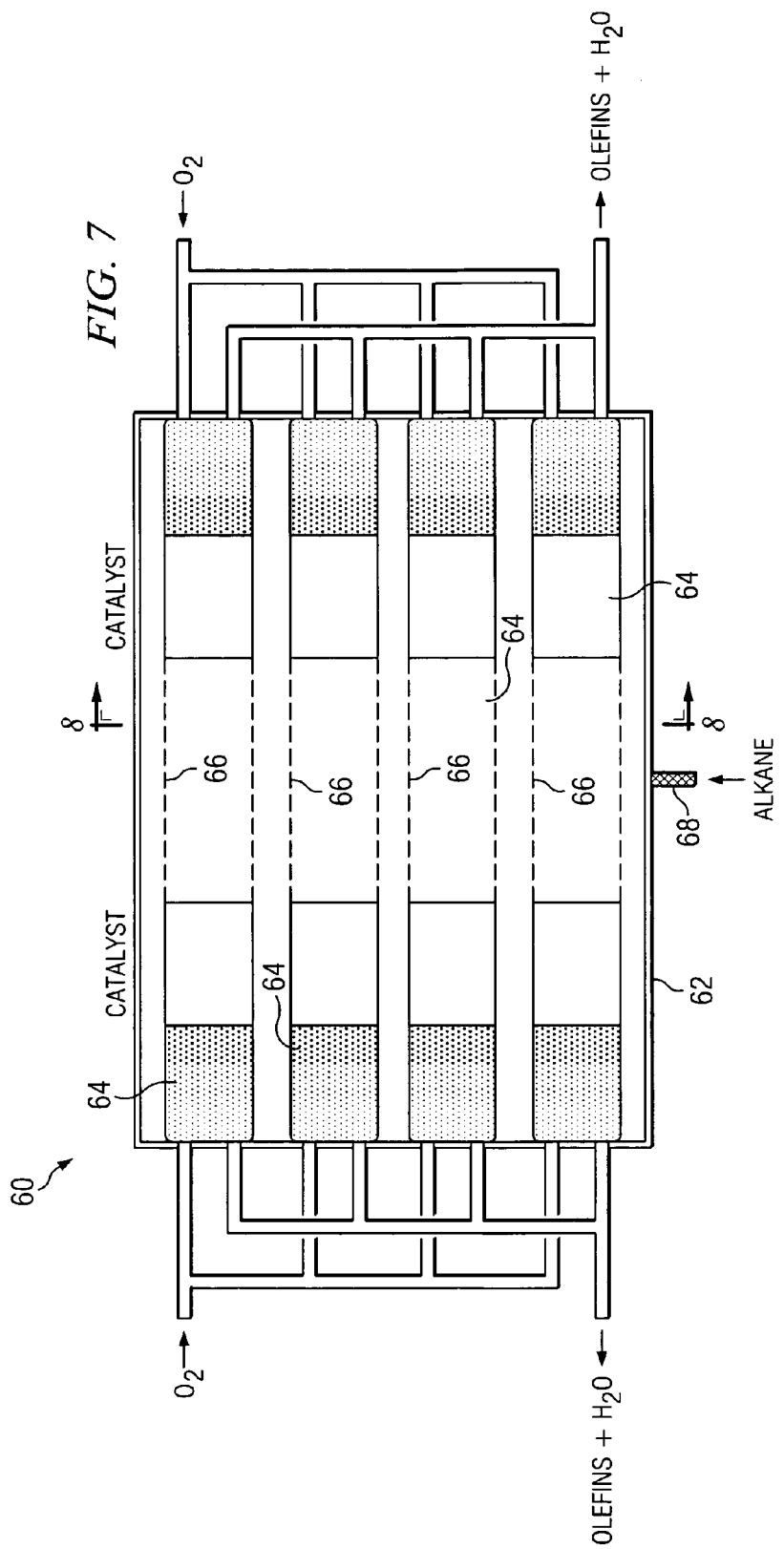
FIG. 7 is a diagrammatic illustration of an apparatus useful in the practice of a variation of the embodiment invention shown in FIG. 3.

Referring now to FIGS. 7, 8, and 9, there is shown an apparatus 60 useful in the practice of the third embodiment of the invention as illustrated in FIGS. 3 and described hereinabove in conjunction therewith. The construction and operation of the apparatus 60 is similar in many respects to the construction and operation of the apparatus 50 as shown in FIGS. 6A and 6B and described hereinabove in conjunction therewith.

The apparatus 60 comprises a barrel 62 having a plurality of cylinders 64 mounted therein. The cylinders 64 are imperforate except that each cylinder 64 has a central portion 66 which is perforated. Alkane is received in the barrel 62 through an inlet 68 and passes from the barrel 62 into the cylinders 64 through the perforations comprising the portions 66 thereof. The pressures of the alkane within the barrel 62 is maintained high enough such that alkane flows into the cylinders 64 while preventing the outflow of reaction products therefrom.

The cylinders 64 of the apparatus 60 are further illustrated in FIG. 9. As indicated above, each cylinder 64 is imperforate except for the perforated portion 66 thereof. The cylinder 64 has end walls 68 and 70 situated at the opposite ends thereof. Each of the end walls 68 and 70 is provided with an oxygen or air receiving passageway 72 and a product discharge passageway 74.

Each cylinder 64 comprises a first zone 76 which initially contains metal halide and a second zone 78 which initially contains metal oxide. A third or central zone 80 receives halide through the perforations comprising the perforated portion 66 of the cylinder 64. Zones 82 located between the zones 76 and 78, respectively, and the zone 80 contain a catalyst.

The catalyst contained within the zone 82 preferably comprises a selected zeolite. The catalyst may also comprise a metal halide/oxide. If employed, the metal halide/oxide of the zones 82 is preferably a different metal halide/oxide as compared with the metal halide/oxide comprising the zones 76 and 78.

Operation of the apparatus 60 is substantially identical to the operation of the apparatus 50 as illustrated in FIGS. 6A and 6B and described hereinabove in conjunction therewith. Oxygen or air is initially directed into the cylinder 64 through the passageway 72. The oxygen or the oxygen from the air reacts with the metal halide within the zone 76 to produce halide and metal oxide. The halide passes into the central zone 80 where it reacts with the alkane therein to produce alkyl halide and hydrogen halide. The alkyl halide and hydrogen halide pass through the catalyst within the zone 82 which facilitates coupling of the molecules comprising the alkyl halide into molecules having larger numbers of carbon atoms. The hydrogen halide and the now-coupled alkyl halide next pass into the zone 78 where the hydrogen halide and coupled alkyl halide react with the metal oxide therein to produce product and water. The product and the water are recovered from the cylinder 64 through the outlet 74.

The foregoing process continues until substantially all of the metal halide within the zone 76 is converted to metal oxide and substantially all of the metal oxide in the zone 78 is converted to metal halide. At this point the direction of flow through the cylinder 64 is reversed with oxygen or air being received through the opening 72 in the end 70 of the cylinder 64 and products and water being recovered through the opening 74 formed in the end 68 of the cylinder 64.

Referring to FIG. 10, there is shown an apparatus 90 useful in the practice of the third embodiment of the invention as illustrated in FIG. 3 and described hereinabove in conjunction therewith. The apparatus 90 comprises the barrel 92 having a heat transfer fluid 94 contained therein. The barrel 92 further comprises a bromination manifold 96 situated at one end thereof and a pair of oxygen receiving/product discharge manifolds 98 and 100 situated at the opposite end thereof.

A baffle 102 is centrally disposed within the barrel 92. A plurality of tubular passageways 104 are situated on one side of the baffle 102 and extend between the oxygen receiving/product discharge manifold 98 and the bromination manifold 96. A plurality of tubular passageways 106 extend between the manifold 96 and the manifold 100.

The tubes 104 are initially packed with metal halide. Oxygen or air is received in the manifold 98 through a passageway 108. The oxygen or the oxygen from the air react with the metal halide within the tubes 104 to produce halide and metal oxide. Halide flows from the tubes 104 into the manifold 96 where it reacts with alkane which is received in the manifold 96 through a passageway 110.

The reaction of the halide with the alkane within the manifold 96 produces alkyl halide and hydrogen halide. The tubes 106 are initially filled with metal oxide. The alkyl halide and the hydrogen halide resulting from the reaction within the manifold 96 pass through the tubes 106 thereby converting the metal oxide contained therein to metal halide and producing products. The products are received in the manifold 100 and are recovered there from through a passageway 112.

As indicated above, the reaction between the oxygen or the oxygen from the air and the metal halide may be endothermic. Conversely, the reaction of the alkyl halide and the hydrogen halide with the metal oxide may be exothermic. It is also possible that, under certain circumstances, the oxidation of the metal halide is an exothermic reaction and/or that the halide/metal oxide reaction is endothermic. The heat transfer fluid 94 within the barrel 92 flows around the baffle 102 as indicated by the arrows 114 thereby transferring heat between the exothermic reaction and the endothermic reaction and in this manner each achieves thermodynamic equilibrium.

The reaction of the oxygen or the oxygen from the air with the metal halide within the tubes 104 continues until substantially all of the metal halide has been converted to metal oxide. Similarly, the reaction of the alkyl halide and the hydrogen halide with the metal oxide within the tubes 106 continues until substantially all of the metal oxide has been converted to metal halide. At this point the direction of flow through the apparatus 90 is reversed with oxygen or air being received through the passageway 112 and products being recovered through the passageway 108.

Figure 11:
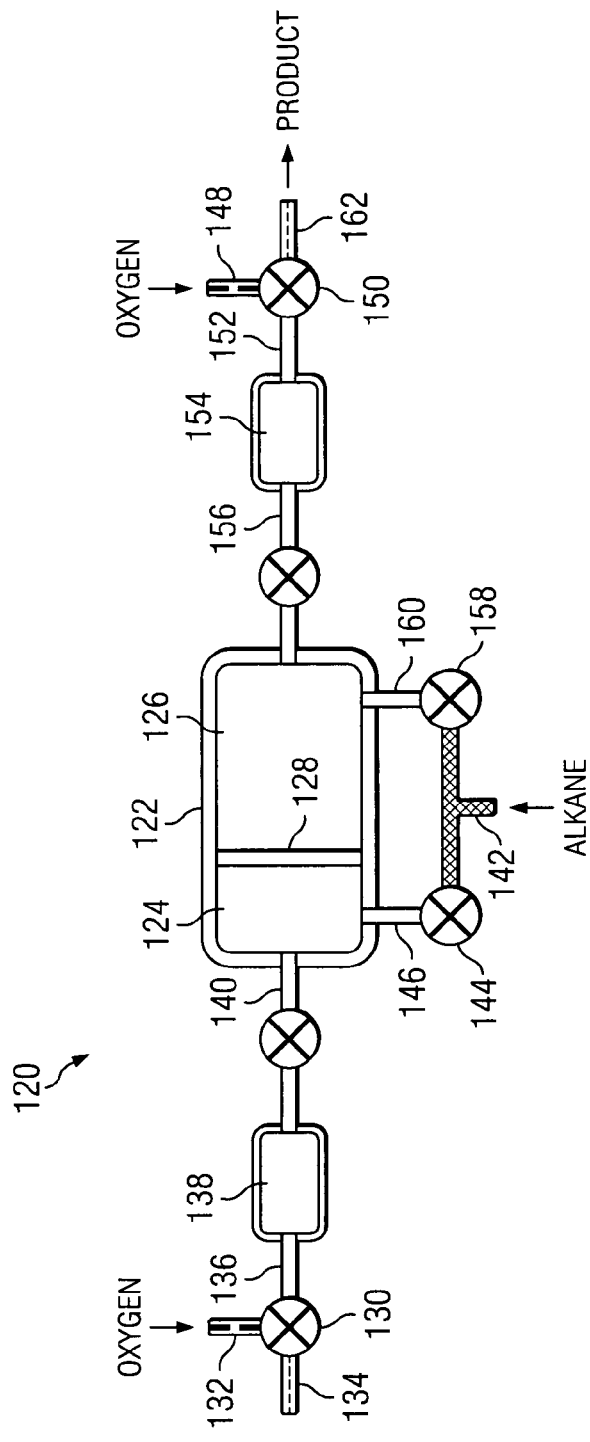
FIG. 11 is the diagrammatic illustration of an apparatus useful in the practice of a fifth embodiment of the invention.
Figure 12A:
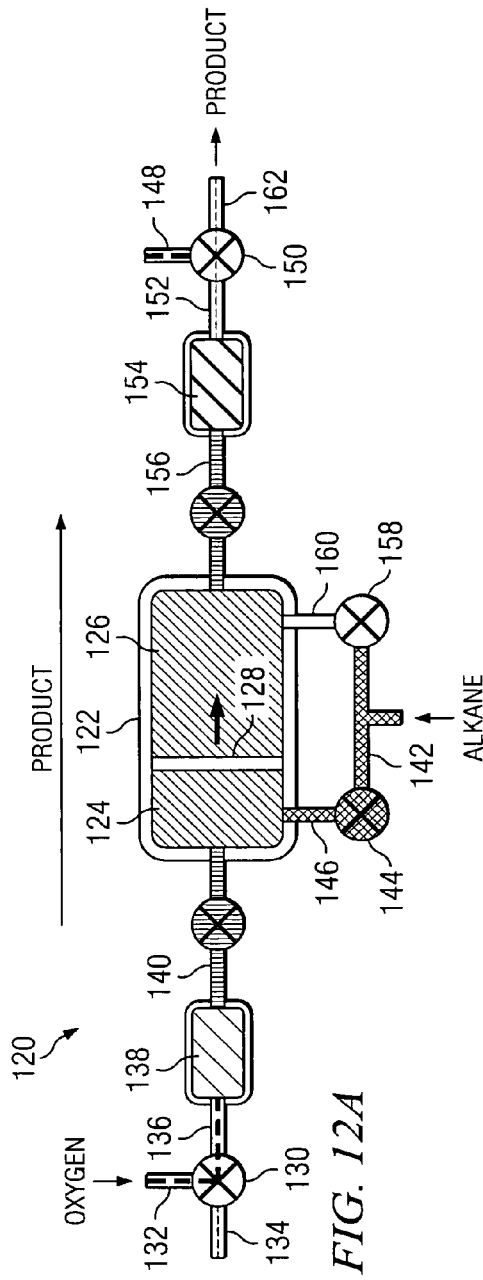
FIG. 12A is an illustration of a first step in the operation of the apparatus of FIG. 11.
Figure 12B:
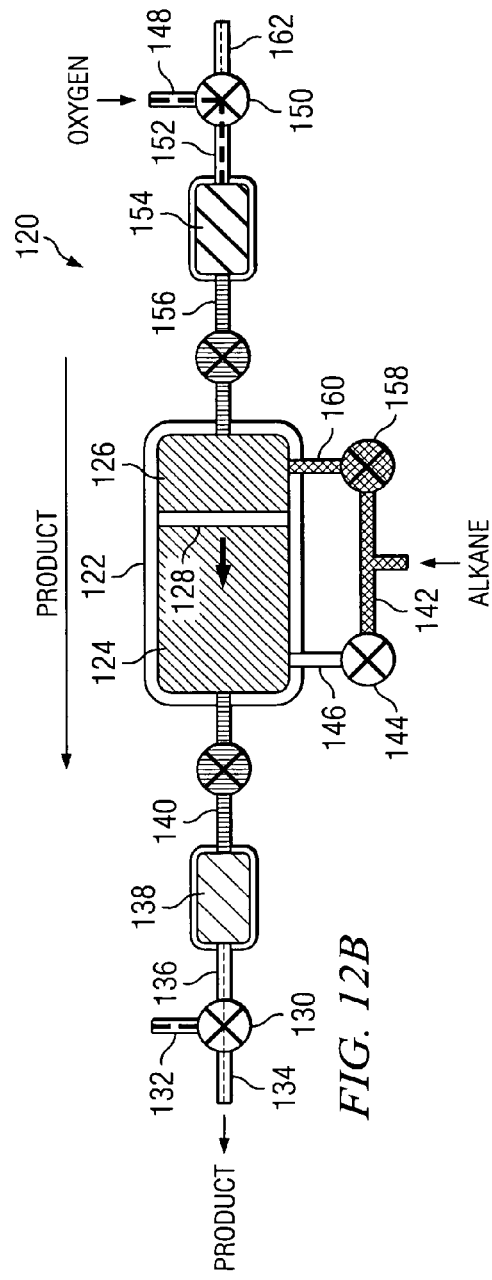
FIG. 12B is an illustration of a later step in the operation of the apparatus of FIG. 11.

Referring to FIGS. 11, 12A, and 12B, there is shown an apparatus 120 which is useful in the practice in the third embodiment of the invention as illustrated in FIG. 3 and described hereinabove in conjunction therewith. The apparatus 20 includes a bromination chamber 122 which is divided into first and second portions 124 and 126 by a piston 128. A valve 130 selectively controls the flow of oxygen or air received through a passageway 132 into the portion 124 of the chamber, or directs the flow of products outwardly from the apparatus 120 through a passageway 134. Oxygen or air entering the apparatus 120 through the passageway 132 and the valve 130 passes through a passageway 136 into a chamber 138 which initially contains metal halide. Within the chamber 138 the oxygen or the oxygen from the air reacts with the metal halide to produce halide and metal oxide. Halide passes from the chamber 138 through a passageway 140 into the portion 124 of the chamber 122.

Alkane is received in the portion 124 of the chamber 122 through a passageway 142, a valve 144, and a passageway 146. Within the portion 124 the alkane reacts with halide produced by the reaction within the chamber 138 to produce alkyl halide and hydrogen halide. As the reaction continues the alkyl halide and the hydrogen halide force the piston 128 to move rightwardly (FIG. 11). This process continues until all of the metal halide within the chamber 138 has been converted to metal oxide and the piston 128 has been forced to the extreme right hand end (FIG. 11) of the chamber 122.

At the beginning of the procedure just described the portion 126 of the chamber 122 was filled with alkyl halide and hydrogen halide. As will be appreciated by those skilled in the art, the presence of alkyl halide and hydrogen halide in the portion 126 resulted from a flow of oxygen or air through a passageway 148, a valve 150, and a passageway 152 into a chamber 154 which was initially filled with metal halide. Reaction of the oxygen or the oxygen from the air with the metal halide produced halide and metal oxide. The halide flowed through a passageway 156 into the portion 126 of the chamber 122 where the halide reacted with alkane received through the passageway 142, and valve 158, and a passageway 160. Within the portion 126 of the chamber 122 the halide reacted with the alkane to produce alkyl halide and hydrogen halide. The production of alkyl halide and hydrogen halide within the portion 126 of the chamber 122 continued until substantially the entire content of the chamber 154 was converted from metal halide to metal oxide.

Referring particularly to FIG. 12A, rightward movement of the piston 128 forces the alkyl halide and the hydrogen halide outwardly from the portion 126 of the chamber 122 through the passageway 156 into the chamber 154. At this point the chamber 154 is filled with metal oxide. The alkyl halide and the hydrogen halide from the portion 126 of the chamber 122 react with the metal oxide in the chamber 154 to produce product and water. The product and water pass through the passageway 152, the valve 150, and a passageway 162 and are recovered.

When the piston 128 has reached the right hand end of the chamber 122, substantially all of the alkyl halide and hydrogen halide have been forced out of the portion 126 of the chamber 122 and have been converted to product by reaction with metal oxide within the chamber 154. At this point substantially all of the metal oxide within the chamber 154 has been converted back to metal halide. The positioning of the valve 150 is reversed thereby admitting oxygen or air into the chamber 154 through the passageway 148, the valve 150, and the passageway 152. Meanwhile, the positioning of the valve 130 is likewise reversed thereby facilitating the recovery of product resulting from the reaction of the alkyl halide and the hydrogen halide within the portion 124 of the chamber 122 with the metal oxide within the chamber 138. Thus, the process is continuous with the piston 128 moving back and forth within the chamber 122 to force previously produced alkyl halide and hydrogen halide outwardly through the metal oxide contained in the associated chamber 138 or 154 to produce product.

Referring to FIGS. 13A and 13B, there is shown an apparatus 170. All of the component parts of the apparatus 170 are identical to components of the apparatus 120 as illustrated in FIGS. 11, 12A, and 12B and described hereinabove in conjunction therewith. Such duplicate component parts are identified in FIGS. 13A and 13B with the same reference numerals utilized above in the description of the apparatus 120.

The apparatus 170 employs duplicate chambers 138 and 154 along with duplicate components controlling the flow of materials to and from the chambers 138 and 154. The use of duplicate chambers 138 and 154 and duplicate components ancillary thereto is useful in increasing the throughput rate of the apparatus 170 as compared with that of the apparatus 120 and/or in balancing the kinetics of the reactions occurring within the chambers 138 and 154.

Figures 15A, 15B:
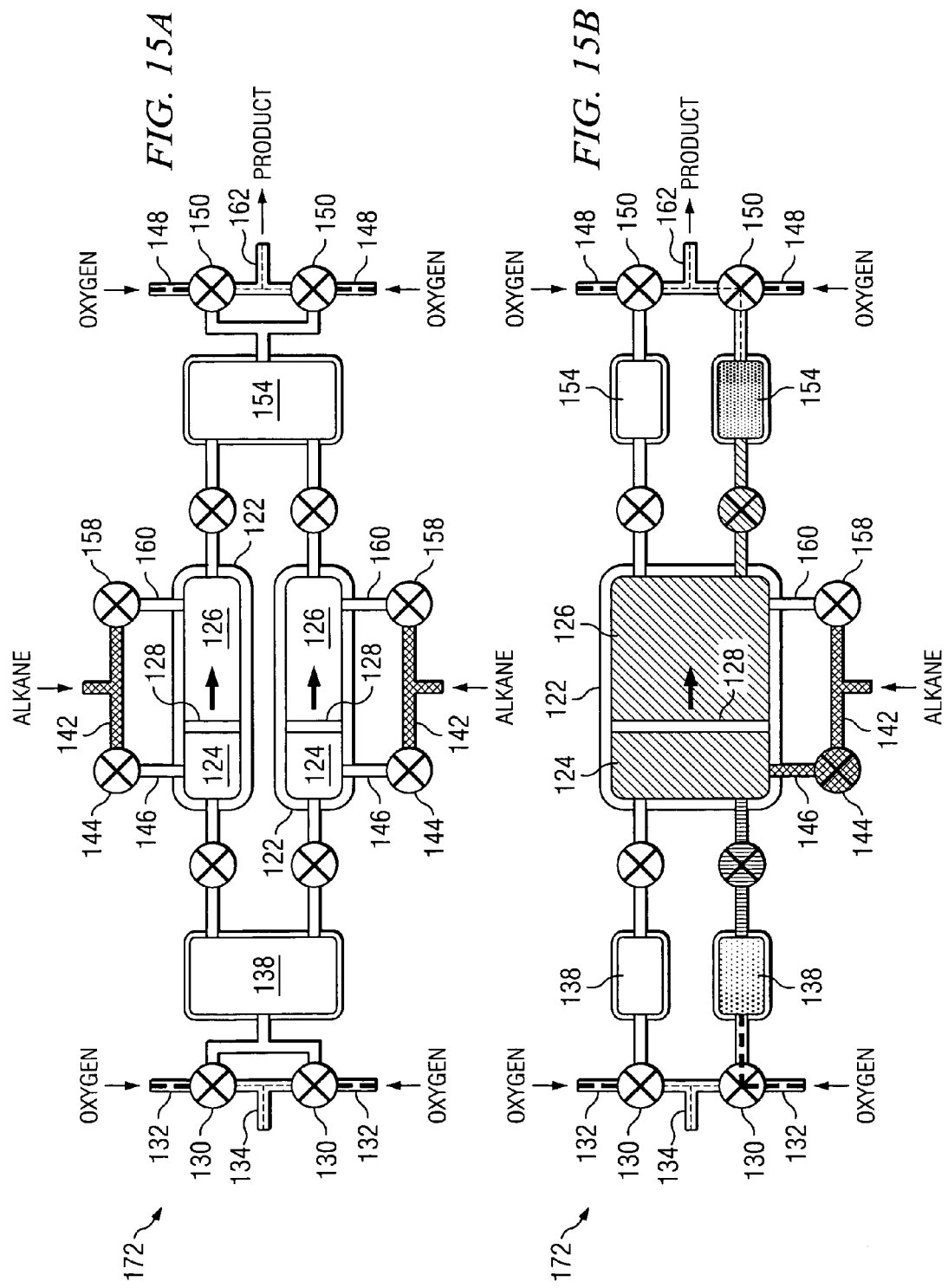
FIG. 15A is a diagrammatic illustration of a first step in the operation of an apparatus comprising a variation of the apparatus illustrated in FIG. 11.
FIG. 15B is an illustration of a later step in the operation of the apparatus of FIG. 15A.

Referring to FIGS. 15A and 15B, there is shown an apparatus 172. All of the component parts of the apparatus 172 are identical to components of the apparatus 120 as illustrated in FIGS. 11, 12A, and 12B and described hereinabove in conjunction therewith. Such duplicate component parts are identified in FIGS. 15A and 15B with the same reference numerals utilized above in the description of the apparatus 120.

The apparatus 172 employs duplicate chambers 122 along with duplicate components controlling the flow of materials to and from the chambers 122. The use of duplicate chambers 122 and duplicate components ancillary thereto is useful in increasing the throughput rate of the apparatus 170 as compared with that of the apparatus 120 and/or in balancing the kinetics of the reactions occurring within the chambers 122.

Although preferred embodiments of the invention have been illustrated in the accompanying Drawing and described in the foregoing Detailed Description, it will be understood that the invention is not limited to the embodiments disclosed but is capable of numerous rearrangements, modifications, and substitutions of parts and elements without departing from the spirit of the invention.

What is claimed is:

1. A method of converting alkanes to corresponding hydrocarbons including the steps of:
   providing a vessel having an unsegregated hollow interior defining a first zone, a second zone, and a third zone;
   reacting metal halide and oxygen in the first zone of the vessel to form metal oxide and halide;
   reacting the halide from the first zone with alkane in the second zone of the vessel to form alkyl halide;
   reacting alkyl halide from the second zone and metal oxide in the third zone of the vessel to form at least one hydrocarbon corresponding to the product of the reaction of the alkyl halide reactant and metal halide;
   transporting the metal halide from the third zone of the vessel to the first zone thereof; and
   recycling metal oxide from the first zone of the vessel to the third zone thereof.

2. A method of converting alkanes to their corresponding hydrocarbons including the steps of:
   providing a vessel having an unsegregated hollow interior defining a first zone, a second zone, and a third zone;
   reacting metal halide and oxygen in the first zone of the vessel to form metal oxide and halide;
   reacting halide from the first zone with alkane in the second zone of the vessel to form alkyl halide;
   reacting alkyl halide from the second zone and metal oxide in the third zone of the vessel to form at least one hydrocarbon corresponding to the product of the reaction of the alkyl halide reactant and metal halide;
transporting the metal oxide from the first zone of the vessel through the vessel to the third zone thereof; and
recycling metal halide from the third zone of the vessel to the first zone thereof.

3. A method of converting alkanes to corresponding hydrocarbons including the steps of:
providing a vessel having an unsegregated hollow interior defining a first zone, a second zone, and a third zone;
initially reacting metal halide and oxygen in the first zone of the vessel to form metal oxide and halide;
reacting halide from the first zone with alkane in the second zone of the vessel to form alkyl halide;
reacting alkyl halide from the second zone and metal oxide in the third zone of the vessel to form at least one hydrocarbon corresponding to the product of the reaction of the alkyl halide reactant and metal halide; subsequently reversing the flow of gases within the vessel and thereafter:
reacting metal halide and oxygen in the third zone of the vessel to form metal oxide and halide;
reacting halide from the third zone with alkane in the second zone of the vessel to form alkyl halide;
reacting alkyl halide from the second zone and metal oxide in the first zone of the vessel to form a reaction product corresponding to the alkyl halide reactant and metal halide.

4. A method of converting alkanes to corresponding hydrocarbons comprising the steps of:
a. providing a substantially imperforate chamber having first and second ends and comprising a first reactant receiving zone located at the first end thereof, a second reactant receiving zone located at the second end thereof, and a centrally disposed reaction zone located between the first reactant receiving zone and the second reactant receiving zone;
b. providing a quantity of metal halide;
c. positioning the quantity of metal halide in the first reactant receiving zone of the chamber;
d. providing a quantity of metal oxide;
e. positioning the quantity of metal oxide in the second reactant receiving zone of the chamber;
f. providing an oxidizing gas;
g. reacting the oxidizing gas with the metal halide and thereby producing gaseous halide and metal oxide;
h. providing a quantity of alkane;
i. directing the alkane into the reaction zone of the chamber;
j. reacting the alkane with the gaseous halide produce in step g. in the reaction zone and thereby producing alkyl halide;
k. reacting the alkyl halide produced in step j. with the metal oxide and thereby producing a non-alkane hydrocarbon and metal halide; and
l. recovering the non-alkane hydrocarbon produced in step k. from the chamber.

5. The method of claim 4 wherein the halide comprising the metal halide of step b. is selected from the group consisting of bromine, chlorine and iodine.

6. The method of claim 4 wherein the oxidizing gas of step f. is selected from the group consisting of oxygen and air.

7. The method of claim 4 wherein the alkane of step h. is selected from the group consisting of methane, ethane, propane, butane, and isobutane.

8. The method of claim 4 wherein the step of providing an alkane is carried out by providing a mixture of at least two alkanes.

9. The method of claim 4 further including the subsequent steps of reacting the metal halide produced in step k. with oxidizing gas and thereby producing gaseous halide and metal oxide and reacting the metal oxide produced in step g. with alkyl halide and thereby producing a non-alkane hydrocarbon and metal halide.

10. The method of claim 4 further characterized by:
providing a first catalyst receiving zone between the first reactant receiving zone and the reaction zone;
providing a second catalyst receiving zone between the reaction zone and the second reactant receiving zone;
providing first and second quantities of a predetermined catalyst; positioning the first quantity of the catalyst in the first catalyst receiving zone; positioning the second quantity of the catalyst in the second catalyst receiving zone;
the catalyst facilitating coupling of the alkyl halide molecules produced in the reaction zone.

11. A method of converting alkanes to corresponding hydrocarbons comprising the steps of:
a. providing a substantially imperforate chamber having first and second ends and comprising a first reactant receiving zone located at the first end thereof, a second reactant receiving zone located at the second end thereof, a centrally disposed reaction zone located between the first reactant receiving zone and the second reactant receiving zone, a first catalyst-receiving zone located between the first reactant receiving zone and the reaction zone, and a second catalyst receiving zone located between the reaction zone and the second reactant receiving zone;
b. providing a quantity of metal halide;
c. positioning the quantity of metal halide in the first reactant receiving zone of the chamber;
d. providing a quantity of metal oxide;
e. positioning the quantity of metal oxide in the second reactant receiving zone of the chamber;
f. providing first and second quantities of a predetermined catalyst;
g. positioning the first quantity of the catalyst in the first catalyst receiving zone;
h. positioning the second quantity of the catalyst in the second catalyst receiving zone;
i. providing an oxidizing gas;
j. reacting the oxidizing gas with the metal halide and thereby producing gaseous halide and metal oxide;
k. providing a quantity of alkane;
l. directing the alkane into the reaction zone of the chamber;
m. reacting the alkane with the gaseous halide produce in step j. in the reaction zone and thereby producing alkyl halide;
n. directing the alkyl halide into engagement with catalyst in the second catalyst receiving zone and thereby facilitating coupling of the alkyl halide molecules;
o. reacting the alkyl halide produced in step m. with the metal oxide and thereby producing a non-alkane hydrocarbon and metal halide; and
p. recovering the non-alkane hydrocarbon produced in step o. from the chamber.

12. The method of claim 11 wherein the halide comprising the metal halide of step b. is selected from the group consisting of bromine, chlorine and iodine.

13. The method of claim 11 wherein the oxidizing gas of step i. is selected from the group consisting of oxygen and air.

14. The method of claim 11 wherein the alkane of step k. is selected from the group consisting of methane, ethane, propane, butane, and isobutane.

15. The method of claim 11 wherein the step of providing an alkane is carried out by providing a mixture of at least two alkanes.

16. The method of claim 11 further including the subsequent steps of reacting the metal halide produced in step o. with oxidizing gas and thereby producing gaseous halide and metal oxide and reacting the metal oxide produced in step j. with alkyl halide and thereby producing a non-alkane hydrocarbon and metal halide.

17. The method of claim 11 wherein the catalyst comprises a predetermined zeolite.

18. A method of converting alkanes to corresponding hydrocarbons comprising the steps of:
 a. providing a chamber having substantially imperforate first and second end sections and a perforated central section and comprising a first reactant receiving zone located in the first end section thereof, a second reactant receiving zone located in the second end section thereof, and a centrally disposed reaction zone located in the perforated central section thereof;
 b. providing a quantity of metal halide;
 c. positioning the quantity of metal halide in the first reactant receiving zone of the chamber;
 d. providing a quantity of metal oxide;
 e. positioning the quantity of metal oxide in the second reactant receiving zone of the chamber;
 f. providing an oxidizing gas;
 g. reacting the oxidizing gas with the metal halide and thereby producing gaseous halide and metal oxide;
 h. providing a quantity of alkane;
 i. directing the alkane through the perforations of the central section of the chamber into the reaction zone;
 j. reacting the alkane with the gaseous halide produce in step g. in the reaction zone and thereby producing alkyl halide;
 k. reacting the alkyl halide produced in step j. with the metal oxide and thereby producing a non-alkane hydrocarbon and metal halide; and
 l. recovering the non-alkane hydrocarbon produced in step k. from the chamber.

19. The method of claim 18 wherein the halide comprising the metal halide of step b. is selected from the group consisting of bromine and chlorine.

20. The method of claim 18 wherein the oxidizing gas of step f. is selected from the group consisting of oxygen and air.

21. The method of claim 18 wherein the alkane of step h. is selected from the group consisting of methane, ethane, propane, butane, and isobutane.

22. The method of claim 18 wherein the step of providing an alkane is carried out by providing a mixture of at least two alkanes.

23. The method of claim 18 further including the subsequent steps of reacting the metal halide produced in step k. with oxidizing gas and thereby producing gaseous halide and metal oxide and reacting the metal oxide produced in step g. with alkyl halide and thereby producing a non-alkane hydrocarbon and metal halide.

24. The method of claim 18 further characterized by:
 providing a first catalyst receiving zone between the first reactant receiving zone and the reaction zone;
 providing a second catalyst receiving zone between the reaction zone and the second reactant receiving zone;
 providing first and second quantities of a predetermined catalyst;
 positioning the first quantity of the catalyst in the first catalyst receiving zone; positioning the second quantity of the catalyst in the second catalyst receiving zone;
 the catalyst facilitating coupling of the alkyl halide molecules produced in the reaction zone.

25. The method of claim 18 including the additional step of providing an enclosure having the chamber enclosed therein and providing a quantity of alkane within the enclosure whereby alkane from the enclosure flows through the perforations of the chamber into the reaction zone.

26. A method of converting alkanes to corresponding hydrocarbons comprising the steps of:
 a. providing an enclosure having first and second ends;
 b. providing a baffle within the enclosure which segregates the enclosure into first and second zones;
 c. providing a heat transfer fluid;
 d. substantially filling the enclosure with the heat transfer fluid;
 e. providing a reaction manifold at one end of the enclosure;
 f. providing an oxidizing gas receiving manifold at the second end of the enclosure;
 g. providing a product receiving manifold at the second end of the enclosure;
 h. providing at least one first imperforate tube;
 l. extending the first tube continuously from the oxidizing gas receiving manifold through the first zone of the enclosure to the reaction manifold;
 j. providing at least one second imperforate tube;
 k. extending the second tube continuously from the bromination manifold through the second zone of the enclosure to the product receiving manifold;
 l. providing a quantity of metal halide;
 m. positioning the quantity of metal halide in the first tube;
 n. providing quantity of metal oxide;
 o. positioning the quantity of metal oxide in the second tube;
 p. providing an oxidizing gas;
 q. directing the oxidizing gas into the oxidizing gas receiving manifold and from the oxidizing gas receiving manifold into the first tube;
 r. reacting the oxidizing gas with the metal halide in the first tube and thereby producing gaseous halide and metal oxide;
 s. providing a quantity of alkane;
 t. directing the alkane into the reaction manifold;
 u. reacting the alkane with the gaseous halide produce in step r. in the reaction manifold and thereby producing alkyl halide;
 v. directing the alkyl halide produced in step u. into the second tube;
 w reacting the alkyl halide produced in step u. with the metal oxide in the second tube and thereby producing a non-alkane hydrocarbon and metal halide;
 x. directing the non-alkane hydrocarbon produced in step w. into the product receiving manifold; and
 y. recovering the non-alkane hydrocarbon produced in step w. from the from the product receiving manifold.

27. The method of claim 26 wherein the halide comprising the metal halide of step l. is selected from the group consisting of bromine and chlorine.

28. The method of claim 26 wherein the oxidizing gas of step p. is selected from the group consisting of oxygen and air.

29. The method of claim 26 wherein the alkane of step s. is selected from the group consisting of methane, ethane, propane, butane, and isobutane.

30. The method of claim 26 wherein the step of providing an alkane is carried out by providing a mixture of at least two alkanes.

31. The method of claim 26 further including the subsequent steps of reacting the metal halide produced in step w. with oxidizing gas and thereby producing gaseous halide and metal oxide and reacting the metal oxide produced in step r. with alkyl halide and thereby producing a non-alkane hydrocarbon and metal halide.

32. A method of converting alkanes to corresponding hydrocarbons comprising the steps of:
 a. providing a first substantially imperforate reactant receiving chamber;
 b. providing a second substantially imperforate reactant receiving chamber;
 c. providing a substantially imperforate reaction chamber;
 d. providing a piston within the reaction chamber, said piston dividing the reaction chamber into first and second zones and moveable within the reaction chamber to expand and contract the first and second reaction zones relative to one another;
 e. providing a quantity of metal halide;
 f. positioning the quantity of metal halide in the first reactant receiving chamber;
 g. providing a quantity of metal oxide;
 h. positioning the quantity of metal oxide in the second reactant receiving chamber;
 i. providing an oxidizing gas;
 j. reacting the oxidizing gas with the metal halide and thereby producing gaseous halide and metal oxide;
 k. providing a quantity of alkane;
 l. directing the alkane into the first reaction zone of the reaction chamber;
 m. reacting the alkane with the gaseous halide produced in step j. in the first reaction zone and thereby producing alkyl halide;
 n. the production of alkyl halide in the first reaction zone causing movement of the piston within the reaction chamber resulting in expansion of the first reaction zone and contraction of the second reaction zone;
 o. the contraction of the second reaction zone resulting from movement of the piston in the reaction chamber causing previously produced alkyl halide to flow from the second reaction zone into the second reactant receiving chamber;
 p. reacting the previously produced alkyl halide with the metal oxide in the second reactant receiving chamber and thereby producing a non-alkane hydrocarbon and metal halide; and
 q. recovering the non-alkane hydrocarbon from the second reactant receiving chamber.

33. The method of claim 32 wherein the halide comprising the metal halide of step e. is selected from the group consisting of bromine, chlorine, and iodine.

34. The method of claim 32 wherein the oxidizing gas of step i. is selected from the group consisting of oxygen and air.

35. The method of claim 32 wherein the alkane of step k. is selected from the group consisting of methane, ethane, propane, butane, and isobutane.

36. The method of claim 32 wherein the step of providing an alkane is carried out by providing a mixture of at least two alkanes.

37. The method of claim 32 further including the subsequent steps of reacting the metal halide produced in step p. with oxidizing gas and thereby producing gaseous halide and metal oxide and reacting the metal oxide produced in step j. with alkyl halide and thereby producing a non-alkane hydrocarbon and metal halide.

* * * * *

UNITED STATES PATENT AND TRADEMARK OFFICE
CERTIFICATE OF CORRECTION

PATENT NO. : 7,230,150 B2  Page 1 of 1
APPLICATION NO. : 10/894165
DATED : June 12, 2007
INVENTOR(S) : Philip Grosso et al.

It is certified that error appears in the above-identified patent and that said Letters Patent is hereby corrected as shown below:

On the Title Page:

Item (56) References Cited, Other Publications, pg. 2, 1st Ref.
        Delete "eet al.", Insert --et al.--

Item (57) Abstract, line 5
        Delete "invention", Insert --invention,--

In the Claims:

Column 12, line 53, Claim 11
        Delete "produce", Insert --produced--

Column 13, line 39, Claim 18
        Delete "produce", Insert --produced--

Column 14, line 30, Claim 26
        Delete "I.", Insert --i--

Column 14, line 40, Claim 26
        After "providing", Insert --a--

Signed and Sealed this

Fifteenth Day of April, 2008

JON W. DUDAS
*Director of the United States Patent and Trademark Office*